United States Patent [19]

Brandes et al.

[11] Patent Number: 5,780,540
[45] Date of Patent: Jul. 14, 1998

[54] DISPERSANTS AND DISPERSANT VISCOSITY INDEX IMPROVERS FROM SELECTIVELY HYDROGENATED POLYMERS

[75] Inventors: Ellen Bernice Brandes, Princeton; Wan-Li Liu, Belle Mead; Frederick Charles Loveless, Princeton, all of N.J.

[73] Assignee: Mobil Oil Corporation, Fairfax, Va.

[21] Appl. No.: 734,982

[22] Filed: Oct. 22, 1996

Related U.S. Application Data

[63] Continuation-in-part of Ser. No. 488,046, Jun. 7, 1995, Pat. No. 5,633,415, which is a continuation-in-part of Ser. No. 382,814, Feb. 3, 1995, Pat. No. 5,545,783, which is a division of Ser. No. 179,051, Jan. 7, 1994, Pat. No. 5,387,730, which is a division of Ser. No. 992,341, Dec. 17, 1992, Pat. No. 5,288,937, which is a continuation of Ser. No. 907,959, Aug. 6, 1992, Pat. No. 5,210,359, which is a division of Ser. No. 466,135, Jan. 16, 1990, Pat. No. 5,149,895.

[51] Int. Cl.$^6$ .................................................. C08F 8/32
[52] U.S. Cl. ......................... 524/572; 524/573; 525/332.8; 525/332.9; 525/333.1; 525/380; 525/381; 525/382; 525/384; 525/385
[58] Field of Search ........................ 525/332.8, 332.9, 525/333.1; 524/572, 573

[56] References Cited

U.S. PATENT DOCUMENTS

| | | |
|---|---|---|
| 3,426,006 | 2/1969 | Nutzel et al. . |
| 3,668,263 | 6/1972 | Morrison et al. . |
| 3,766,215 | 10/1973 | Hesse et al. . |
| 3,823,109 | 7/1974 | Middlebrook . |
| 3,823,203 | 7/1974 | De La Mare . |
| 3,830,880 | 8/1974 | De La Mare . |
| 3,868,330 | 2/1975 | Meinhardt et al. . |
| 4,007,121 | 2/1977 | Holder et al. . |
| 4,137,185 | 1/1979 | Gardiner et al. . |
| 4,234,435 | 11/1980 | Meinhardt et al. . |
| 4,557,847 | 12/1985 | Gutierrez et al. . |
| 4,767,553 | 8/1988 | Hart et al. . |
| 4,843,120 | 6/1989 | Halasa et al. . |
| 4,879,349 | 11/1989 | Hoxmeier . |
| 5,147,570 | 9/1992 | VanZon et al. . |
| 5,149,895 | 9/1992 | Coolbaugh et al. . |
| 5,187,236 | 2/1993 | Coolbaugh et al. . |
| 5,210,359 | 5/1993 | Coolbaugh et al. . |
| 5,229,464 | 7/1993 | Erickson et al. . |
| 5,242,989 | 9/1993 | Bening et al. . |
| 5,244,980 | 9/1993 | Gibler et al. . |
| 5,268,427 | 12/1993 | Coolbaugh et al. . |
| 5,276,100 | 1/1994 | Coolbaugh et al. . |
| 5,288,937 | 2/1994 | Coolbaugh et al. . |
| 5,292,820 | 3/1994 | Coolbaugh et al. . |
| 5,306,780 | 4/1994 | Coolbaugh et al. . |
| 5,352,743 | 10/1994 | Coolbaugh et al. . |
| 5,359,009 | 10/1994 | Coolbaugh et al. . |
| 5,376,722 | 12/1994 | Coolbaugh et al. . |
| 5,387,730 | 2/1995 | Coolbaugh et al. . |
| 5,399,629 | 3/1995 | Coolbaugh et al. . |
| 5,416,163 | 5/1995 | Coolbaugh et al. . |
| 5,438,102 | 8/1995 | Brandes et al. . |
| 5,457,161 | 10/1995 | Coolbaugh et al. . |
| 5,470,914 | 11/1995 | Coolbaugh et al. . |
| 5,510,548 | 4/1996 | Coolbaugh et al. . |
| 5,530,068 | 6/1996 | Coolbaugh et al. . |
| 5,545,783 | 8/1996 | Coolbaugh et al. . |
| 5,552,492 | 9/1996 | Brandes et al. . |
| 5,569,718 | 10/1996 | Coolbaugh et al. . |
| 5,585,441 | 12/1996 | Coolbaugh et al. . |

FOREIGN PATENT DOCUMENTS

| | | |
|---|---|---|
| 0315280 | 5/1989 | European Pat. Off. . |
| 0 344 021 A2 | 11/1989 | European Pat. Off. . |
| 0 677 065 | 1/1994 | European Pat. Off. . |
| 0 632 074 A2 | 1/1995 | European Pat. Off. . |
| 3414657 | 12/1984 | Germany . |
| 56-127604 | 10/1981 | Japan . |
| 328729 | 7/1989 | Japan . |
| 2020670 | 11/1979 | United Kingdom . |
| WO 94/15973 | 7/1994 | WIPO . |

OTHER PUBLICATIONS

Wang et al., "Functionalized PMS/IB Copolymers Offer Wide Range of Properties," *Elastomerics*, 14–19 (Jan. 1992).
Wang et al. "Functionalized PMS/IB Copolymers Offer Wide Range of Properties—Part II", *Elastomerics*, 22–26 (Feb. 1992).
Fusco et al., Isobutylene–Based Polymers in Tires—Status and Future Trends *Rubber World*, 34–39 and 42 (May 1992).
Kruse, D.F. "A New Brominated Butyl Rubber," *Automotive Polymers* &, 17–20 ( ).
Edwards, D. C., "Developments in Butyl/Halobutyl Vulcanization Benefit Performance", *Elastomerics* (1989).
Falk, *Journal of Polymer Science: Part A–1*, vol. 9, 2617–2623 (1971).
Falk et al., *Die Angewandte Makromolekulare Chemie 21*, (No. 236), 17–23 (1972).
Mohajer et al., *Polymer*, vol. 23, 1523–1535 (Sep. 1982).

*Primary Examiner*—Bernard Lipman
*Attorney, Agent, or Firm*—Lori F. Cuomo; Dennis P. Santini

[57] ABSTRACT

The invention provides dispersants and dispersant viscosity index improvers which include polymers of conjugated dienes which have been hydrogenated and functionalized. The dispersant substances include compositions including a copolymer of two different conjugated dienes, a copolymer of a p-alkylstyrene and a conjugated diene, or a homopolymer of a conjugated diene. The polymers are selectively hydrogenated to produce polymers which have highly controlled amounts of unsaturation, permitting highly selective functionalization. Also provided are lubricant fluids, such as mineral and synthetic oils, which have been modified in their dispersancy and/or viscometric properties by means of the dispersant substances of the invention. Also provided are methods of modifying the dispersancy and/or viscometric properties of lubricating fluids such as mineral and synthetic lubricating oils. The dispersant substances may also include a carrier fluid to provide dispersant concentrates.

57 Claims, No Drawings

DISPERSANTS AND DISPERSANT VISCOSITY INDEX IMPROVERS FROM SELECTIVELY HYDROGENATED POLYMERS

CROSS-REFERENCE TO RELATED APPLICATIONS

The application is a continuation in part of U.S. application Ser. No. 08/488,046, filed Jun. 7, 1995, now U.S. Pat. No. 5,633,415, which is a continuation in part of U.S. application Ser. No. 08/382,814, filed Feb. 3, 1995, now U.S. Pat. No. 5,545,783, which is a divisional of application Ser. No. 08/179,051 filed Jan. 7, 1994, now U.S. Pat. No. 5,387,730 which is a divisional of application Ser. No. 07/992,341, filed Dec. 17, 1992, and now U.S. Pat. No. 5,288,937, which is a continuation of application Ser. No. 07/907,959 filed Aug. 6, 1992, and now U.S. Pat. No. 5,210,359, which is a divisional of application Ser. No. 07/466,135 filed Jan. 16, 1990, and now U.S. Pat. No. 5,149,895. The entire contents of application Ser. No. 07/466,135 are incorporated herein by reference.

BACKGROUND OF THE INVENTION

This invention relates to dispersants, dispersants with Viscosity index (VI) improving properties, and dispersant VI improvers from functionalized diene polymers, and methods of their use. More particularly, the invention relates to dispersants, dispersants with VI improving properties, and dispersant VI improvers from selectively hydrogenated copolymers prepared using conjugated dienes. The invention is additionally directed to dispersants, dispersants with VI improving properties, and dispersant VI improvers from chemically modified derivatives of the above polymers.

Liquid elastomers are well known and are used in various applications. For example, many functionally terminated polybutadiene liquid elastomers are known. These materials are generally highly unsaturated and frequently form the base polymer for polyurethane formulations. The preparation and application of hydroxy-terminated polybutadiene is detailed by J. C. Bross et al. in "Hydroxyl-terminated polymers obtained by free radical polymerization—Synthesis, characterization and applications," *Advances in Polymer Science* 81, Springer-Verlag, Berlin, Heidelberg, 1987, pp. 167–220.

Also, liquid polymers possessing acrylate, carboxy- or mercapto-terminals are known. In addition to butadiene, it is known to utilize isoprene as the base monomer for the liquid elastomers. The liquid elastomers may contain additional monomers, such as styrene or acrylonitrile, for controlling compatibility in blends with polar materials, such as epoxy resin.

Also shown in the prior art are pure hydrocarbon, non-functionalized liquid rubbers. These liquid elastomers contain varying degrees of unsaturation for utilization in vulcanization. Typical of highly unsaturated liquid elastomers is polybutadiene, e.g., that sold under the name RICON by Ricon Resins, Inc. A liquid polyisoprene which has been hydrogenated to saturate 90% of its original double bonds is marketed as LIR-290 by Kuraray Isoprene Chemical Co. Ltd. Still more highly saturated are liquid butyl rubbers available from Hardman Rubber Co., and Trilene, a liquid ethylene-propylene-diene rubber (EPDM) available from Uniroyal Chemical Co. The more highly saturated liquid elastomers exhibit good oxidation and ozone resistance properties.

Falk, *Journal of Polymer Science: PART A-1*, 9:2617–23 (1971), the entire contents of which are incorporated herein by reference, discloses a method of hydrogenating 1,4-polybutadiene in the presence of 1,4-polyisoprene. More particularly, Falk discloses hydrogenation of the 1,4-polybutadiene block segment in the block copolymer of 1,4-polybutadiene—1,4-polyisoprene—1,4-polybutadiene and in random copolymers of butadiene and isoprene, with both polymerized monomers having predominantly 1,4-microstructure. Hydrogenation is conducted in the presence of hydrogen and a catalyst made by the reaction of organoaluminum or lithium compounds with transition metal salts of 2-ethylhexanoic acid. Falk, *Die Angewandte Chemie*, 21(286):17–23 (1972), the entire contents of which are also incorporated herein by reference, discloses the hydrogenation of 1,4-polybutadiene segments in a block copolymer of 1,4-polybutadiene-1,4-polyisoprene-1,4-polybutadiene.

Hoxmeier, Published European Patent Application 88202449.0, filed on Nov. 2, 1988, Publication Number 0 315 280, published on May 10, 1989, discloses a method of selectively hydrogenating a polymer made from at least two different conjugated diolefins. One of the two diolefins is more substituted in the 2, 3 and/or 4 carbon atoms than the other diolefin and produces tri- or tetra-substituted double bond after polymerization. The selective hydrogenation is conducted under such conditions as to hydrogenate the ethylenic unsaturation incorporated into the polymer from the lesser substituted conjugated diolefin, while leaving unsaturated at least a portion of the tri- or tetra-substituted unsaturation incorporated into the polymer by the more substituted conjugated diolefin.

Mohajer et al., "Hydrogenated linear block copolymers of butadiene and isoprene: Effects of variation of composition and sequence architecture on properties", *Polymer* 23:1523–35 (1982) discloses essentially completely hydrogenated butadiene-isoprene-butadiene (HBIB), HBI and HBI block copolymers in which butadiene has predominantly 1,4-microstructure.

Kuraray K K, Japanese published patent application Number JP-328 729, filed on Dec. 12, 1987, published on Jul. 4, 1989, discloses a resin composition comprising 70–99% wt. of a polyolefin (preferably polyethylene or polypropylene) and 1–30% wt. of a copolymer obtained by hydrogenation of at least 50% of unsaturated bond of isoprene/butadiene copolymer.

Ashless dispersants are additives to lubricant fluids such as fuels and lubricating oils which improve the dispersability of the fluids or improve their viscometric properties. Typically, such dispersants are modified polymers, having an oleophilic polymer backbone to assure good solubility and to maintain particles suspended in the oil, and polar functionality to bind or attach to oxidation products and sludge. Dispersants generally have a solubilizing oleophilic (hydrophobic) tail and a polar (hydrophilic) head, forming micelles when actively bound to sludge.

Common dispersants include polyisobutenes which have been modified by the ene reaction to include functional groups such as succinimides, hydroxyethyl imides, succinate esters/amides, and oxazolines. Other dispersants include Mannich base derivatives of polybutenes, ethylene propylene polymers, and acrylic polymers.

Traditionally, dispersants have been polybutenes functionalized at one site in the molecule via an ene reaction with maleic anhydride followed by imidization with a polyamine. The polybutenes are typically 500–2,000 in molecular weight, and due to the polymerization process employed in their manufacture, have no more than one olefin per polybutene molecule. Accordingly, the number of potential functional groups per chain is limited to about one. Typically, this site is at a terminal portion of the molecule. Moreover, it is generally accepted that, in order to obtain beneficial dispersant properties, a molecule must have at least one functional group per approximately 2,000 molecular weight. Consequently, the molecular weight of traditional polybutene dispersants cannot exceed 2,000 if the desire functionality/hydrocarbon ratio is to be maintained. In addition, traditional dispersants have had molecular structures which have limited the placement of functional groups, generally requiring that such groups be placed at the terminal regions of the molecules.

The polymerization process for the traditional butene polymers has also generated products having an unacceptably wide distribution of molecular weights, i.e., an unacceptably high ratio of weight average molecular weight ($M_w$) to number average molecular weight ($M_n$). Typically, such distributions are $M_w/M_n \geq ~2.5$, producing compositions whose dispersant properties are now well defined.

Moreover, functionalization reactions in these polymers have typically yielded substantial quantities of undesirably by-products such as insoluble modified polymers of variant molecular weight. Functionalization reactions can also result in compounds which contain undesirable chemical moieties such as chlorine.

U.S. Pat. No. 4,007,121 to Holder et al. describes lubricant additives which include polymers such as ethylene propylene polymers (EPT) having N-hydrocarbylcarboxamide groups.

European Patent Application No. EP 0 344 021 discloses polymers prepared from p-alkylstyrene and isobutylene. This document discloses that the polymerization proceeds optimally when the amount of diene in the reaction mixture is minimized. No description is provided as to whether such compounds would serve as lubricant additives.

U.S. Pat. Nos. 3,868,330 and 4,234,435 to Meinhardt et al. disclose carboxylic acid acylating agents for modification of lubricant additives. Modified polyalkenes are described such as polyisobutene-substituted succinic acylating agents having $M_n$ of 1300–5000 and $M_w/M_n$ of 1.5–4. These process employ chlorination which results in residual chlorine in the polymer, creating an environmental hazard.

Heretofore, the art has failed to produce dispersants and dispersant VI improvers having selective and controllable amounts of polar functionality in their polymeric structure. Thus, the art has failed to provide any means of developing dispersants and dispersant VI improvers having higher molecular weights and/or higher amounts of functionalization per molecule. The art has also failed to provide dispersant polymers having desirably narrow molecular weight distributions to avoid the presence of by-products which degrade dispersant performance. The art has also failed to provide dispersant and VI improving compositions which exhibit good thermal stability.

Accordingly, it is a purpose of this invention to provide dispersants and dispersant VI improvers having polymeric structures which permit highly selective control of the degree of unsaturation and consequent functionalization. Unique materials can also be obtained by chemical modification of the polymers of this invention since the polymers can be selectively modified at controllable sites, such as at random sites or at the terminal ends of the molecules.

It is an additional purpose of this invention to provide a method for the production of dispersants and dispersant VI improvers from polymers having controlled amounts of unsaturation incorporated randomly in an otherwise saturated backbone. In contrast to EPDM-based dispersants, the level of unsaturation can be inexpensively and easily controlled, e.g., from 1% to 50%, to provide a wide variation in functionalizability.

It is a further purpose of the invention to provide dispersant and VI improving polymers having narrow molecular weight distributions and a concomitant lack of undesirably by-products, thereby providing more precisely tailored dispersant and/or VI improving properties.

SUMMARY OF THE INVENTION

The invention provides dispersant and dispersant Viscosity index (VI) improvers which include polymers of conjugated dienes which have been hydrogenated and subsequently chemically modified. The dispersancy and VI improving properties of the compositions of the invention may be controlled by controlling the size of the polymers and the extend and distribution of their functionalization. Accordingly, these substances are termed throughout "dispersant substances".

In one embodiment of the invention, there is provided a dispersant substance for modifying the dispersancy or viscometric properties of a lubricant fluid, in which the dispersant substance includes a copolymer of two different conjugated dienes. In this case, the first conjugated diene includes at least one relatively more substituted conjugated diene having at least five carbon atoms and the formula:

wherein $R^1$–$R^6$ are each hydrogen or a hydrocarbyl group, provided that at least one of $R^1$–$R^6$ is a hydrocarbyl group, and also provided that, after polymerization, the unsaturation of the polymerized conjugated diene of formula (1) has the formula:

wherein $R^I$, $R^{II}$, $R^{III}$ and $R^{IV}$ are each hydrogen or a hydrocarbyl group, provided that either both $R^I$ and $R^{II}$ are hydrocarbyl groups or both $R^{III}$ and $R^{IV}$ are hydrocarbyl groups.

The second conjugated diene in the dispersant substances of this embodiment includes at least one relatively less substituted conjugated diene which is different from the first conjugated diene and has at least four carbon atoms and the formula:

wherein $R^7$–$R^{12}$ are each hydrogen or a hydrocarbyl group, provided that, after polymerization, the unsaturation of the polymerized conjugated diene of formula (3) has the formula:

wherein $R^V$, $R^{VI}$, $R^{VII}$ and $R^{VIII}$ are each hydrogen or a hydrocarbyl group, provided that one of $R^V$ or $R^{VI}$ is hydrogen, one of $R^{VII}$ or $R^{VIII}$ is hydrogen, and at least one of $R^V$, $R^{VI}$, $R^{VII}$ and $R^{VIII}$ is a hydrocarbyl group.

Following polymerization the diene copolymer is preferably functionalized by a method which includes selectively hydrogenating the copolymer to provide a selectively hydrogenated copolymer, followed by functionalizing the selectively hydrogenated copolymer to provide a functionalized copolymer having at least one polar functional group and modifying the functionalized copolymer by reaction with a Lewis base selected from the group consisting of a monoamine, polyamine, polyhydroxy compound, reactive polyether, or a combination thereof.

In a preferred embodiment, the dispersant substance includes a polymer in which the first and second conjugated dienes are polymerized as a block copolymer including at least two alternating blocks:

$$(I)_x-(B)_y$$

or $$(B)_y-(I)_x)$$

In this case, the block (I) includes at least one polymerized conjugated diene of formula (1), while the block (B) includes at least one polymerized conjugated diene of formula (3). In addition, x is the number of polymerized monomer nits in block (I) and is at least 1, and y is the number of polymerized monomer units in block (B) and is at least 25. It should be understood throughout that x and y are defined relative to blocks in a linear block copolymer or blocks in an arm or segment of a branched or star-branched copolymer in which the arm or segment has substantially linear structure.

Preferably, in the block copolymers of this embodiment, x is from about 1 to about 600, and y is from about 30 to about 4,000, more preferably x is from about 1 to about 350, and y is from about 30 to about 2,800. While larger values for x and y are generally related to larger molecular weights, polymers which have multiple blocks and star-branched polymers typically will have molecular weights which are not well represented in the values of x and y for each block.

Alternatively, the dispersant substance includes the first and second conjugated dienes polymerized as a random copolymer. The dispersant substance may include the first and second conjugated dienes polymerized as a branched or star-branched copolymer.

The copolymers useful according to this embodiment typically have a molecular weight of at least about 2,000. Preferably, the molecular weight of these polymers is from about 2,000 to about 1,000,000, more preferably from about 5,000 to about 500,000.

The molecular weight of a polymer of the invention is generally associated with the physical properties it exhibits when employed as a dispersant or dispersant VI improver. Typically, polymers having lower molecular weights are employed as dispersants, while VI-improving properties and relative thickening power are associated with polymers having higher molecular weights and correspondingly greater viscosity. For purposes of discussion, polymers of the invention having molecular weights in the range of from about 2,000 to about 20,000 may be classified as dispersants, polymers having molecular weights of from about 20,000 to about 50,000 may be classified as dispersants with VI-improving properties, and polymers having molecular weights of about 50,000 or more may be classified as dispersant VI improvers.

In the dispersant substances of the invention, the copolymer is preferably selectively hydrogenated. It is preferred that the unsaturation of formula (4) be substantially completely hydrogenated, thereby retaining substantially none of the original unsaturation of this type, while the unsaturation of formula (2) is substantially retained (i.e., the residual unsaturation after hydrogenation), in at least an amount which is sufficient to permit functionalization of the copolymer.

After the hydrogenation reaction, the Iodine Number for the residual unsaturation of formula (2) is generally from about 50% to about 100% of the Iodine Number prior to the hydrogenation reaction. More preferably, after hydrogenation, the Iodine Number for the residual unsaturation of formula (2) is about 100% of the Iodine Number prior to the hydrogenation reaction.

After the hydrogenation reaction, the Iodine Number for the residual unsaturation of formula (4) is from about 0% to about 10% of the Iodine Number prior to the hydrogenation reaction. More preferably, after the hydrogenation reaction, the Iodine Number for the residual unsaturation of formula (4) is from about 0% to about 0.5% of the Iodine Number prior to the hydrogenation reaction. Most preferably, after the hydrogenation reaction, the Iodine Number for the residual unsaturation of formula (4) is from about 0% to about 0.2% of the Iodine Number prior to the hydrogenation reaction.

The conjugated diene of formula (1) preferably includes a conjugated diene such as isoprene, 2,3-dimethyl-butadiene, 2-methyl-1,3-pentadiene, myrcene, 3-methyl-1,3-pentadiene, 4-methyl-1,3-pentadiene, 2-phenyl-1,3-pentadiene, 2-phenyl-1,3-pentadiene, 3-phenyl-1,3-butadiene, 2,3-dimethyl-1,3-pentadiene, 2-hexyl-1,3-butadiene, 3-methyl-1,3-hexadiene, 2-benzyl-1,3-butadiene, 2-p-tolyl-1,3-butadiene, or mixtures thereof. More preferably, the conjugated diene of formula (1) includes isoprene, myrcene, 2,3-dimethyl-butadiene or 2-methyl-1,3-pentadiene. Still more preferably, the conjugated diene of formula (1) includes isoprene.

Preferably, the conjugated diene of formula (3) includes 1,3-butadiene, 1,3-pentadiene, 1,3-hexadiene, 1,3-heptadiene, 2,4-heptadiene, 1,3-octadiene, 2,4-octadiene, 3,5-octadiene, 1,3-nonadiene, 2,4-nonadiene, 3,5-nonadiene, 1,3-decadiene, 2,4-decadiene, 3,5-decadiene, or mixtures thereof. More preferably, the conjugate diene of formula (3) includes 1,3-butadiene, 1,3-pentadiene, or 1,3-hexadiene. Still more preferably, the conjugated diene of formula (3) includes 1,3-butadiene.

Generally, when the conjugated diene includes substantial amounts of 1,3-butadiene, the polymerized butadiene includes a mixture of 1,4- and 1,2-units. The preferred structures contain at least about 25% of the 1,2-units. More preferably, the structures contain from about 30% to about 90% of the 1,2-subunits. Most preferably, the structures contain from about 45% to about 65% of the 1,2-units.

To provide dispersancy, the selectviely hydrogenated polymer is chemically modified of "functionalized" to provide a polymer having at least one polar functional group, such as, but not limited to, halogen, epoxy, hydroxy, amino, nitrilo, mercapto, imido, carboxy, and sulfonic acid groups of combinations thereof. The functionalized polymers can be further modified to give a more desired type of functionality.

In a preferred case, the selectively hydrogenated polymer is chemically modified by a method which includes: reacting the selectively hydrogenated polymer with an unsaturated carboxylic acid (or derivative thereof, such as maleic anhydride) to provide an acylated polymer, and then reacting the acylated polymer with a monoamine, a polyamine, a polyhydroxy compound, a reactive polyether, or a combination thereof.

In another preferred embodiment, the invention provides dispersant substances based upon a copolymer of at least one ring-substituted styrene and at least one conjugated diene. Preferably, the ring-substituted styrene has at least one benzylic hydrogen and the formula:

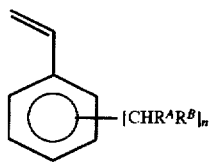

(5)

wherein n=1–5, and $R^A$ and $R^B$ are each hydrogen or a hydrocarbyl group. Preferably, n=1–3, and more preferably n=1. Preferably, the conjugated diene comprises at least one conjugated diene having at least four carbon atoms and a formula corresponding to the conjugated dienes of formulae (1) or (3) described above. Following polymerization, the original unsaturation in the polymerized conjugated diene has a formula corresponding to formulae (2) or (4) as described above.

Following polymerization the substituted styrene-diene copolymer is preferably functionalized by a method which includes selectively hydrogenating the copolymer to provide a selectively hydrogenated copolymer, following by functionalizing the selectively hydrogenated copolymer to provide a functionalized copolymer having at least one polar functional group.

The polymers of this embodiment include a ring-substituted styrene in an amount of from about 0.5% wt. to about 25% wt., and a conjugated diene in an amount of from about 75% wt. to about 99.5% wt. Preferably, a ring-substituted styrene is included in an amount of from about 1% wt. to about 20% wt., and a conjugated diene in an amount of from about 80% to about 99% wt. More preferably, a ring-substituted styrene is included in an amount of from about 5% wt. to about 15% wt., and a conjugated diene is included in an amount of from about 85% to about 95% wt.

In the dispersant substances of this embodiment, a ring-substituted styrene and a conjugated diene are preferably polymerized as a block copolymer comprising at least two alternating blocks:

$(P)_x-(B)_y$ or $(B)_y-(P)_x$ wherein the block (P) includes at least one polymerized ring-substituted styrene of formula (5), and the block (B) includes at least one polymerized conjugated diene of formulae (1) or (3). In addition, x is the number of polymerized monomer units in block (P) and is at least 1, and y is the number of polymerized monomer units in block (B) and is at least 25. Preferably, in the block copolymers of this embodiment, x is from about 1 to about 600, and y is from about 30 to about 4,000, more preferably x is from about 1 to about 350, and y is from about 30 to about 2,800.

Alternatively, a ring-substituted styrene and a conjugated diene are polymerized as a random copolymer. In addition, a ring-substituted styrene and a conjugated diene may be polymerized as a branched or star-branched random or block copolymer.

The copolymers useful according to this embodiment typically have a molecular weight of at least about 2,000. Preferably, the molecular weight of these polymers is from about 2,000 to about 1,000,000, more preferably from about 5,000 to about 500,000. The molecular weight distribution of these polymers is preferably about 1.01 to about 1.20.

The dispersant substances of this embodiment include a copolymer which can be selectively hydrogenated to retain as much of the original aromatic unsaturation a possible, while removing as much of the original unsaturation of formulae (2) or (4) as possible. Preferably, following hydrogenation, the residual unsaturation of formulae (2) or (4) is from about 0% to about 1% of the Iodine Number prior to the hydrogenation reaction. More preferably, after the hydrogenation reaction, the Iodine Number for the residual unsaturation of formulae (2) or (4) is from about 0% to about 0.5% of the Iodine Number prior to the hydrogenation reaction. Most preferably, after the hydrogenation reaction, the Iodine Number for the residual unsaturation of formulae (2) or (4) is about 0% of the Iodine Number prior to the hydrogenation reaction.

Preferably, following the selective hydrogenation, the aromatic unsaturation of the substituted styrene monomer is at least about 50% retained, more preferably at least about 90% retained, and most preferably about 100% retained.

In the dispersant substances of this embodiment, the ring-substituted styrene component of the polymer preferably includes an alkylstyrene, such as vinyl toluene, vinyl xylene, methylstyrene, ethylstyrene, propylstyrene, isopropylstyrene, sec-butylstyrene, or benzylstyrene, or mixtures thereof. More preferably, the ring-substituted styrene includes p-methylstyrene.

In the dispersant substances of this embodiment, the conjugated diene may include one or more conjugated dienes of formulae (1) or (3) as described elsewhere herein. Preferably, the conjugated diene includes a conjugated diene of formula (1) such as isoprene, 2,3-dimethyl-butadiene, 2-methyl-1,3-pentadiene, myrcene, 3-methyl-1,3-pentadiene, 4-methyl-1,3-pentadiene, 2-phenyl-1,3-butadiene, 2-phenyl-1,3-pentadiene, 3-phenyl-1,3 pentadiene, 2,3-dimethyl-1,3-pentadiene, 2-hexyl-1,3-butadiene, 3-methyl-1,3-hexadiene, 2-benzyl-1,3-butadiene, 2-p-tolyl-1,3-butadiene, or mixtures thereof, and/or a conjugated diene of formula (3) such as 1,3-butadiene, 1,3-pentadiene, 2,4-hexadiene, 1,3-hexadiene, 1,3-heptadiene, 2,4-heptadiene, 1,3-octadiene, 2,4-octadiene, 3,5-octadiene, 1,3-nonadiene, 2,4-nonadiene, 3,5-nonadiene, 1,3-decadiene, 2,4-decadiene, 3,5-decadiene, or mixtures thereof.

More preferably, the conjugated diene of formula (1) includes isoprene, myrcene, 2,3-dimethyl-butadiene, or 2-methyl-1,3-pentadiene. Most preferably, the conjugated diene of formula (1) includes isoprene. More preferably, the conjugated diene of formula (3) includes 1,3-butadiene, 1,3-pentadiene, or 1,3-hexadiene. Most preferably, the conjugated diene of formula (3) includes 1,3-butadiene.

In the copolymers of this embodiment, when the conjugated diene includes 1,3-butadiene, the polymerized butadiene include a mixture of 1,4- and 1,2-units. Preferably, the conjugated dienes include at least about 25%, more preferably from about 30% to about 90%, and most preferably from about 45% to about 65%, of the 1,2-units.

Also in this embodiment, the selectively hydrogenated polymer is more preferably chemically modified to provide a polymer with at least one halogen functional group.

Preferably, the halogen functional group includes bromine. To impart dispersant properties, it is more preferred to further modify the polymer, e.g., by reacting the halogen group with an amine, a polyamine, a polyhydroxy compound, a reactive polyether or a combination thereof.

In still another embodiment, the invention is directed to homopolymers of a conjugated diene, selected from among any of the dienes of formulae (1) and (3) described above. Preferred conjugated dienes of formula (1) include isoprene, myrcene, 2,3-dimethyl-butadiene, or 2-methyl-1,3-pentadiene. Preferred conjugated dienes of formula (3) include 1,3-butadiene or 1,3-pentadiene. The polymerized diene may be prepared in linear, branched, or star-branched form. The homopolymer may be subjected to selective hydrogenation to provide a partially hydrogenated polymer, retaining a sufficient amount of the original unsaturation to functionalize the polymer.

Any of the dispersant substances of the invention may include a functionalized polymer of the invention distributed in a carrier fluid such as a synthetic or mineral oil, to provide a dispersant concentrate. The dispersant concentrates generally include the polymer in an amount of from about 5% wt. to about 90% wt., more preferably from about 10% wt. to about 70% wt., of the dispersant substance, depending upon the molecular weight of the polymer.

The dispersant substances may further include at least one additive selected from the group consisting of antioxidants, pour point depressants, detergents, dispersants, friction modifiers, anti-wear agents, anti-foam agents, corrosion and rust inhibitors, Viscosity index improvers, and the like.

The invention further provides a method of modifying the dispersancy or viscometric properties of a fluid such as a lubricant. The method includes admixing with a fluid an amount of a dispersant substance of the invention which is sufficient to provide a dispersant-modified fluid having dispersancy or viscometric properties which are altered from the original fluid. Preferably, the method involves admixing the dispersant substance in an amount of from about 0.001% wt. to about 20% wt., more preferably from about 0.1% wt. to about 10% wt., and most preferably from about 0.5% wt. to about 7% wt., of the dispersant-modified fluid. Typically, the method of the invention is employed to modify lubricating oils and normally liquid fuels; such as motor oils, transmission fluids, hydraulic fluids, gear oils, aviation oils, and the like. In addition, the method may further include admixing with the fluid at least one additive such as antioxidants, pour point depressants, detergents, dispersants, friction modifiers, anti-wear agents, anti-foam agents, corrosion and rush inhibitors, viscosity index improvers, and the like.

The invention also provides a dispersant-modified fluid, such as a hydrocarbon fluid, having modified dispersancy or viscometric properties. In this embodiment, the dispersant-modified fluid typically includes a mineral or synthetic oil and a dispersant substance of the invention. Preferably, the dispersant-modified fluid of the invention includes a dispersant substance in an amount of from about 0.001% wt. to about 20% wt., more preferably from about 0.1% wt. to about 10% wt., and most preferably from about 0.5% wt. to about 7% wt., of the modified lubricating fluid. The dispersant-modified fluid preferably includes a mineral or synthetic lubricating oil or a normally liquid fuel; such as motor oils, transmission fluids, hydraulic fluids, gear oils, aviation oils, and the like. These dispersant-modified fluids may further include at least one additive such as antioxidants, pour point depressants, detergents, dispersants, friction modifiers, anti-wear agents, anti-foam agents, corrosion and rust inhibitors, viscosity index improvers, and the like.

The polymers of all embodiments are prepared under anionic polymerization conditions. Following polymerization, the polymers of the invention are selectively hydrogenated to provide a controlled amount and extent of residual unsaturation. After the selective hydrogenation reaction, the hydrogenation catalyst is removed from the polymer and the polymer is chemically modified of functionalized to impart desirable characteristics for the dispersant substances of the invention.

Accordingly, as a result of the invention, there are now provided dispersants, dispersants with VI-improving properties, and dispersant VI improvers prepared by polymerization of conjugated dienes, followed by selective hydrogenation and functionalization. These dispersant substances of the invention possess numerous advantages, including controlled molecular weight, controlled molecular weight distribution, controlled polymer structure, variable and controlled amounts and distribution of functionality, superior thermal stability, potentially permitting reduced treat levels and yielding benefits such as improved viscometric properties.

These and other advantages of the present invention will be appreciated from the detailed description and examples which are set forth herein. The detailed description and examples enhance the understanding of the invention, but are not intended to limit the scope of the invention.

DETAILED DESCRIPTION OF THE INVENTION

The polymeric dispersants of the invention, typically having lower molecular weights, can be employed in any lubricant or fuel composition that requires a dispersant to control the deposition of sludge particles on, for example, engine parts. Other polymeric substances of the invention, typically those having higher molecular weights, may be employed for their VI-improving properties in any lubricant fluid which may benefit from a modification of its viscometric properties. These compounds may also find a variety of uses in addition to lubricant additives, such as adhesives, sealants, impact modifiers, and the like.

As noted above, traditional dispersants have been polybutenes functionalized via an ene reaction with maleic anhydride followed by imidization with a polyamine. The polybutenes are typically 500–2,000 in molecular weight. With one olefin per polybutene molecule, the number of potential functional groups per chain is limited to one. Consequently, the molecular weight of polybutene may not exceed 2,000 if the desired functionality/hydrocarbon ratio is to be maintained.

By contrast, with this invention, the amount of residual unsaturation can be controllably varied. As a result, the amount of functionality one wishes to incorporate is quite flexible. In addition, the molecular weight of the polymer backbone is not limited to 2,000. Higher molecular weight polymers can be prepared and functionalized such that the same functionality/hydrocarbon ratio that is found in the traditional dispersant is maintained if so desired. Moreover, with this invention, the position of the functionality is not limited to the end of the polymer chain as it is with polybutenes. Instead, a variety of options is now available, including, for example, randomly along the backbone, at one end, at both ends, or in the center, of the polymer chain.

If a polymer according to the invention is of sufficiently high molecular weight (e.g., 20,000–50,000), it will exhibit increased thickening power and viscosity index-improving (VI-improving) properties, as well as sludge dispersing ability. Hence, the use of these materials may permit reduction in use of both traditional dispersants and VI. If materials are prepared with backbones that are ≧50,000 in molecular weight, the functionalized versions can be classified as dispersant VI improvers or VI improvers with dispersant properties. Their dispersant capabilities are outstanding for dispersant VI improvers.

In one embodiment, the present invention provides polymers including at least two different conjugated dienes, wherein one of the dienes is more substituted in the 2, 3, and 4 carbon positions than the other diene. The more substituted diene produces vinylidene, tri-, or tetra-substituted double bonds after polymerization. Hydrogenation of the material is done selectively so as to saturate the lesser substituted olefins, which primarily arise from the lesser substituted diene, while leaving a portion of the more substituted conjugated olefins behind for functionalizing.

In this embodiment, the more substituted conjugated diene will have at least five (5) carbon atoms and the following formula:

wherein $R^1$–$R^6$ are each hydrogen (H) or a hydrocarbyl group, provided that at least one of $R^1$–$R^6$ is a hydrocarbyl group. After polymerization, the unsaturation in the polymerized conjugated diene of formula (1) has the following formula:

wherein $R'$, $R''$, $R'''$ and $R^{IV}$ are each hydrogen or a hydrocarbyl group, provided that either both $R'$ and $R''$ are hydrocarbyl groups or both $R'''$ and $R^{IV}$ are hydrocarbyl groups. Examples of conjugated dienes of formula 1 include isoprene, 2,3-dimethylbutadiene, 2-methyl-1,3-pentadiene, myrcene, and the like. Isoprene is highly preferred.

The lesser substituted conjugated diene in this embodiment differs from the other diene in that it has at least four (4) carbon atoms and the following formula:

wherein $R^7$–$R^{12}$ are each hydrogen or a hydrocarbyl group. After polymerization, the unsaturation in the polymerized conjugated diene of formula (3) has the following formula:

wherein $R^V$, $R^{VI}$, $R^{VII}$ and $R^{VIII}$ are each hydrogen (H) or a hydrocarbyl group, provided that one of $R^V$ or $R^{VI}$ is hydrogen, one of $R^{VII}$ or $R^{VIII}$ is hydrogen, and at least one of $R^V$, $R^{VI}$, $R^{VII}$ and $R^{VIII}$ is a hydrocarbyl group. Examples of the conjugated diene of formula (3) include 1,3-butadiene, 1,3-pentadiene, 2,4-hexadiene, and the like. A highly preferred conjugated diene of formula 3 is 1,3-butadiene.

An exception to this scheme would be when a tetra-substituted diene, e.g., 2,3-dimethylbutadiene, is used for the more substituted component (1). When this occurs, a tri-substituted olefin, e.g., isoprene, may be used for the lesser substituted component (3), such that one or both of $R^V$ and $R^{VI}$ are hydrogen and both $R^{VII}$ and $R^{VIII}$ are hydrocarbyl.

It will be apparent to those skilled in the art that in the original unsaturation of formula (2), $R'$, $R''$, $R'''$ and $R^{IV}$ may all be hydrocarbyl groups, whereas in the original unsaturation of formula (4) at least one of $R^V$, $R^{VI}$, $R^{VII}$ and $R^{VIII}$ must be a hydrogen.

The hydrocarbyl group or groups in the formulae (1) to (4) are the same or different and they are substituted or unsubstituted alkyl, alkenyl, cycloalkyl, cycloalkenyl, aryl, alkaryl, or aralkyl groups, or any isomers thereof.

The copolymers of this embodiment are prepared by anionically polymerizing a diene of formula (1) at a level of from about 0.5% wt. to about 25% wt., and a diene of formula (3) at a level of from about 75% wt. to about 99.5% wt., in a hydrocarbon solvent using an alkyllithium catalyst. The two monomers can be polymerized in block, tapered block, or random fashion. Since the polymerization is anionic, the molecular weight distribution of these copolymers is typically very narrow, generally ranging from about 1.01 to about 1.20, and is determined by the ratio of monomer to initiator and/or by the presence of coupling agents.

The monomers (1) and (3) may be polymerized either simultaneously or in stepwise fashion depending on the desired position of the remaining unsaturation after hydrogenation. If random positioning of the unsaturation is desired, both monomers are reacted together to give a random copolymer. If it is desirable to have the functionality on only one end, then the monomers are reacted in stepwise fashion, the order being determined as desired, to provide a diblock copolymer. If functionality is need on both ends, then a conjugated diene of formula (1) is polymerized first, followed by a diene of formula (3). To the living anion, a coupling agent, e.g., phenyl benzoate or methyl benzoate, is then added to yield a desired triblock copolymer. Alternatively, a diene of formula (1) may be added to the living diblock to give the triblock. A fourth approach would allow the functionality to be positioned in the center of the polymer chain. In this case, a diene of formula (3) is polymerized first, followed by a diene of formula (1), and then a third block of diene of formula (3) is added by coupling agent or through the living anion of the diblock. In addition, combinations of the above approaches may be employed.

The present invention also includes copolymers that are prepared from a ring-substituted styrene and a conjugated diene, preferably p-methylstyrene and 1,3-butadiene. More specifically, the materials are generated by anionically polymerizing a ring-substituted styrene (about 0.5 wt. % to about 25 wt. %) and a diene (about 99.5 wt. % to about 75 wt. %). The monomers can be polymerized either in block, tapered block, or random fashion. For a random distribution of the ring-substituted styrene, it is necessary to polymerize the two monomers in the presence of a substantial quantity of a polar modifier or to slowly add the diene to polymerizing ring-substituted styrene.

The scope of this embodiment includes ring-substituted styrenes that have at least one benzylic hydrogen and possess the formula:

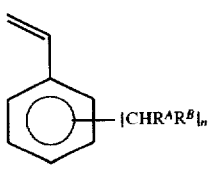

(5)

wherein n=1–5, and $R^A$ and $R^B$ are independently hydrogen or an alkyl group. More preferably, n=1–3, and most preferably n=1. The conjugated diene in this embodiment may be selected from among the dienes having formula (1) or (3) as described elsewhere herein.

This embodiment includes functionalized versions of the ring-substituted styrene-conjugated diene copolymers described above. Functionality-introducing reactions such as halogenation are carried out on the copolymers in a separate post-hydrogenation step. The halogenated copolymers are then further modified, typically by a reaction involving a monoamine or a polyamine, a polyhydroxy compound, a reactive polyether, or a combination thereof.

The invention is further directed to homopolymers of a conjugated diene. The conjugated diene may be selected from any of the dienes described in relation to formulae (1) and (3) described elsewhere herein. These polymers have preferably been partially hydrogenated such that they possess an Iodine Number of 1–150, preferably 2–100. The unsaturation remaining after hydrogenation is used to incorporate polar functionality along the backbone of the polymer. These functionalized materials may be used as lubricant additives. Functionalization may be accomplished by reacting with an unsaturated carboxylic acid derivative via the ene reaction or via a radical addition. Preferably, the acylated polymer is then further modified by reacting with a monoamine or a polyamine. Other modification methods such as halogenation, epoxidation, hydroxylation, and the like, may be used.

The invention can include polymers of differing microstructures. The presence of polar modifier increases the activity of the catalyst and, therefore, increase the level of 1,2-microstructure over 1,4-microstructure in polybutadiene, for example. The percentage of vinyl obtained is directly proportional to the concentration of the modifier employed. Since the reaction temperature also plays a role in determining the microstructure of polybutadiene, the level of modifier must be chosen taking into account the combined effects. Antkowiak et al. have presented a way for quickly determining the proper conditions for preparation of any 1,2-microstructure content within a range of from about 10% to about 80%. Use of this method or any others to achieve the desired microstructure will be known to anyone who is skilled in the art.

The dispersants and idspersant VI improvers of the invention can include different polymer macrostructures. Polymers may be prepared and utilized having linear and/or nonlinear, e.g., star-branched, macrostructures. The star-branched polymers can be prepared by addition of divinylbenzene or the like to the living polymer anion. Lower levels of branching can be obtained through the use of tri-functional or tetra-functional coupling agents, such as tetrachlorosilane.

The invention also includes dispersant polymer wherein the polymers include an additional aryl-substituted olefin such as styrene, p-methylstyrene, vinyl naphthalene, etc. The aryl substituted olefin may be incorporated randomly throughout the polymer, randomly in one or two of the blocks with another monomer, or in a tapered block or pure block at any position along the polymer. Thus, any of the (I) and (B) blocks may include an aryl-substituted olefin in an amount of up to about 30% wt. The random copolymers and homopolymers of the invention can also include an aryl-substituted olefin in an amount of up to about 30% wt.

If an aryl-substituted olefin is incorporated into a higher molecular weight polymer of the invention in a pure block or tapered block fashion, the resulting material will have reduced cold flow. A lack of cold flow is a trait which is desirable for higher molecular weight VI improvers since the bulk polymer resists flowing at temperatures at which it would normally be stored prior to use in a lube oil (e.g., up to about 140° F.). It is generally preferred that the VI improver have a crumb or particulate form which retains its shape during storage. Also, the retention of the shape of the crumbs enhances the ease of solubilization of the polymers because their relatively large surface area is preserved.

In all embodiments of this invention, whenever a reference is made to the "original double bond" or the "original unsaturation" of the block or random polymer (or copolymer), it is understood to mean the double bond(s) in the polymer prior to the hydrogenation reaction. By contrast, the terms "residual double bond(s)" and "residual unsaturation", as used herein, refer to the unsaturated group (s), typically excluding aromatic unsaturation, present in the copolymer after the selective hydrogenation reaction.

The molecular structure of the original or residual double bonds can be determined in any conventional manner, as is known to those skilled in the art, e.g., by infrared (IR) or nuclear magnetic resonance (NMR) analysis. In addition, the total original or residual unsaturation of the polymer can be quantified in any conventional manner, e.g., by reference to the Iodine Number of the polymer.

In any polymers of any of the embodiments of this invention, the microstructure of the polymerized conjugated diene of formula (3) must be such that the polymer is not excessively crystalline after the selective hydrogenation reaction. That is, after the selective hydrogenation reaction the polymer must retain its elastomeric properties, e.g., the polymer should contain not more than about 10% of polyethylene crystallinity. Generally, problems of crystallinity occur only when the polymer includes polymerized 1,3-butadiene. Limiting polymeric crystallinity may be accomplished in various ways. For example, this is accomplished by introducing side branches into the polymerized conjugated dienes of formulae (1) and/or (3), e.g., by controlling the microstructure of 1,3-butadiene if it is the predominant monomer in the diene of formula (3); by using a mixture of dienes of formula (3) containing less than predominant amounts of 1,3-butadiene; or by using a single diene of formula (3), other than 1,3-butadiene. More particularly, if the conjugated diene(s) of formula (3) is predominantly (at least 50% by mole) 1,3-butadiene, the side branches are introduced into the polymer by insuring that the polymerized diene of formula (3) contains a sufficient amount of the 1,2-units to prevent the selectively hydrogenated polymer from being excessively crystalline. Thus, if the conjugated diene of formula (3) is predominantly (at least 50% by mole, e.g., 100% by mole) 1,3-butadiene, the polymerized diene of formula (3), prior to the selective hydrogenation reaction, must contain not more than about 75% wt., preferably from about 10% wt. to about 70% wt., and most preferably from about 35% wt. to about 55% wt. of the 1,4-units, and at least about 25% wt., preferably from about 30% wt. to about 90% wt., and most preferably from about 45% wt. to about 65% wt. of the 1,2-units. If the polymerized diene(s) of formula (3) contains less than 50% by mole of 1,3-butadiene, e.g., 1,3-pentadiene is used as the only diene of formula (3), the microstructure of the polymerized diene of formula (3) prior to the selective hydrogenation reaction is not critical since, after hydrogenation, the resulting polymer will contain substantially no crystallinity.

In all embodiments of the invention, mixtures of dienes of formulae (1) or (3) may be used to prepare block copolymers $(I)_x$-$(B)_y$, or any of the random copolymers or star-branched block and random polymers of the invention. Similarly, mixtures or aryl-substituted olefins may also be used to prepare block, random, or star-branched copolymers of this invention. Accordingly, whenever a reference is made herein to a diene of formulae (1) or (3), or to an aryl-substituted olefin, it may encompass more than one diene of formulae (1) or (3), respectively, and more than one aryl-substituted olefin.

The block copolymers of this invention comprise two or more alternating blocks, identified above. Linear block copolymers having two blocks and block copolymers having three or more blocks are contemplated herein. However, star-branched block polymers containing any combination and number of blocks (I) and (B), or (P) and (B), are also contemplated herein.

The block polymers useful according to the invention typically include at least one block which is substantially completely saturated, while also including at least one block containing controlled levels of unsaturation providing a hydrocarbon elastomer with selectively positioned unsaturation for subsequent functionalization. For the copolymers prepared from two different conjugated dienes, it has been found the that two dienes in the copolymers hydrogenate at different rates, permitting selective control of the placement of residual unsaturation. For copolymers prepared from a ring-substituted styrene and a conjugated diene, it has been found that aromatic unsaturation and the olefinic unsaturation hydrogenate at different rates, again permitting control and placement of the residual unsaturation.

Many variations in composition, molecular weight, molecular weight distribution, relative block lengths, microstructure, branching, and $T_g$ (glass transition temperature) attainable with the use of anionic techniques employed in the preparation of our polymers will be obvious to those skilled in the art.

While not wishing to limit the molecular weight range of liquid elastomers prepared according to our invention, the minimum molecular weight for these liquid polymers is at least about 2,000, preferably about 2,000 to about 50,000, and most prefeably about 5,000 to about 35,000. The star-branched block and random copolymers and homopolymers of this invention may have substantially higher molecular weights and still retain liquid properties. The minimum weight for solid polymers of this invention is at least about 50 to about 1,000,000. The block copolymers of this invention are functionalizable. Without wishing to be bound by any theory of operability, it is believed that they can be functionalized in a controlled manner through the unsaturated groups on the terminal blocks to provide dispersants and dispersant VI improvers having almost uniform distribution of molecular weights. The star-branched and linear versions of the random copolymers and homopolymers of this invention are also functionalizable.

All numerical values of molecular weight given in this specification and the drawings are of number average molecular weight ($M_n$).

The invention will be described hereinafter in terms of the embodiments thereof summarized above. However, it will be apparent to those skilled in the art, that the invention is not limited to these particular embodiments, but, rather, it covers all the embodiments encompassed by the broadest scope of the description of the invention.

Copolymers from at Least Two Dissimilar Conjugated Dienes

In this embodiment of the invention, there are provided copolymers of two dissimilar conjugated dienes, preferably isoprene and 1,3-butadiene. The two monomers can be polymerized by anionic polymerization process in either a block, tapered block, or random fashion.

Th copolymers of this embodiment include a first conjugated diene having at least five (5) carbon atoms and the following formula:

(1)

wherein $R^1$–$R^6$ are each hydrogen or a hydrocarbyl group, provided that at least one of $R^1$–$R^6$ is a hydrocarbyl group, and further provided that, when polymerized, the structure of the double bond in the polymerized conjugated diene of formula (1) has the following formula:

(2)

wherein $R^I$, $R^{II}$, $R^{III}$ and $R^{IV}$ are each hydrogen or a hydrocarbyl group, provided that either both $R^I$ and $R^{II}$ are hydrocarbyl groups or both $R^{III}$ and $R^{IV}$ are hydrocarbyl groups. In the double bond of the polymerized conjugated diene of formula (2), $R^I$, $R^{II}$, $R^{III}$ and $R^{IV}$ may all be hydrocarbyl groups.

The polymers of this embodiment also include a second conjugated diene, different from the first conjugated diene, having at least four (4) carbon atoms and the following formula:

(3)

wherein $R^7$–$R^{12}$ are each hydrogen or a hydrocarbyl group, provided that the structure of the double bond in the polymerized conjugated diene of formula (3) has the following formula:

(4)

wherein $R^V$, $R^{VI}$, $R^{VII}$ and $R^{VIII}$ are each hydrogen (H) or a hydrocarbyl group, provided that one of $R^V$ or $R^{VI}$ is hydrogen, one of $R^{VII}$ or $R^{VIII}$ is hydrogen, and at least one of $R^V$, $R^{VI}$, $R^{VII}$ and $R^{VIII}$ is a hydrocarbyl group.

Following polymerization the diene copolymer of this embodiment is preferably functionalized by a method which includes selectively hydrogenating the copolymer to provide a selectively hydrogenated copolymer, followed by functionalizing the selectively hydrogenated copolymer to provide a functionalized copolymer having at least one polar functional group.

The polymers of this embodiment include a first conjugated diene of formula (1) in an amount of from about 0.5% wt. to about 25% wt., and a second conjugated diene in an amount of from about 75% wt. to about 99.5% wt. Preferably, a first conjugated diene is included in an amount of from about 1% wt. to about 20% wt., and a second conjugated diene in an amount of from about 80% to about 99% wt. More preferably, a first conjugated diene is included in an amount of from about 5% wt. to about 15% wt., and a second conjugated diene is included in an amount of from about 85% to about 95% wt.

The polymers of this embodiment include block copolymers having at least two alternating blocks:

$$(I)_x\text{-}(B)_y$$

or $$(B)_y\text{-}(I)_x.$$

In this case, the polymer includes at least one block (I). The block (I) is a block of at least one polymerized conjugated diene of formula (1) as described above. These block copolymers also include at least one polymerized block (B). The block (B) is a block of at least one polymerized conjugated diene of formula (3) described above.

In the block copolymers of this embodiment, x is at least 1, preferably from about 1 to about 600, and most preferably from about 1 to about 350. The above definition of x means that each of the (I) blocks is polymerized from at least 1, preferably about 1–600, and more preferably about 1–350, monomer units.

In the block copolymers of this embodiment, y is at least 25, preferably from about 30 to about 4,000, more preferably from about 30 to about 2,800. The above definition of y means that each of the (B) blocks is polymerized from at least 25, preferably about 30–4,000, and more preferably about 30–2,800, monomer units.

The block copolymer comprises about 0.5 to about 25%, preferably about 1 to about 5% by wt. of the (I) blocks, and about 75 to about 99.5%, preferably about 95 to about 99% by wt. of the (B) blocks.

In any of the copolymers of this embodiment, the structures of the double bonds defined by formulae (2) and (4) are necessary to produce copolymers which can be selectively hydrogenated in the manner described herein, to produce the selectively hydrogenated block and random copolymers of this invention.

The hydrocarbyl group or groups in the formulae (1) and (2) are the same or different and they are substituted or unsubstituted alkyl, alkenyl, cycloalkyl, cycloalkenyl, aryl, alkaryl, or aralkyl groups, or any isomers thereof. Suitable hydrocarbyl groups are alkyls of 1–20 carbon atoms, alkenyls of 1–20 carbon atoms, cycloalkyls of 5–20 carbon atoms, aryls of 6–12 carbon atoms, alkaryls of 7–20 carbon atoms or aralkyls of 7–20 carbon atoms. Examples of suitable alkyl groups are methyl, ethyl, propyl, butyl, pentyl, hexyl, heptyl, octyl, decyl, methyl-decyl or dimethyl-decyl. Examples of suitable alkenyl groups are ethenyl, propenyl, butenyl, pentenyl or hexenyl. Examples of suitable cycloalkyl groups are cyclohexyl or methylcyclohexyl. Examples of suitable cycloalkenyl groups are 1-, 2-, or 3-cyclohexenyl or 4-methyl-2-cyclohexenyl. Examples of suitable aryl groups are phenyl or diphenyl. Examples of suitable alkaryl groups are 4-methyl-phenyl (p-tolyl) or p-ethyl-phenyl. Examples of suitable aralkyl groups are benzyl or phenethyl. Suitable conjugated dienes of formula (1) used to polymerize the (I) block are isoprene, 2,3-dimethyl-butadiene, 2-methyl-1,3-pentadiene, myrcene, 3-methyl-1,3-pentadiene, 4-methyl-1,3-pentadiene, 2-phenyl-1,3-butadiene, 2-phenyl-1,3-pentadiene, 3-phenyl-1,3 pentadiene, 2,3-dimethyl-1,3-pentadiene, 2-hexyl-1,3-butadiene, 3-methyl-1,3-hexadiene, 2-benzyl-1,3-butadiene, 2-p-tolyl-1,3-butadiene, or mixtures thereof, preferably isoprene, myrcene, 2,3-dimethyl-butadiene, or 2-methyl-1,3-pentadiene, and most preferably isoprene.

The hydrocarbyl group or groups in the formula (3) may or may not be the same as those in formula (4). These hydrocarbyl groups are the same as those described above in conjunction with the discussion of the hydrocarbyl groups of formulae (1) and (2). Suitable monomers for the (B) block are 1,3-butadiene, 1,3-pentadiene, 2,4-hexadiene, 1,3-hexadiene, 1,3-heptadiene, 2,4-heptadiene, 1,3-octadiene, 2,4-octadiene, 3,5-octadiene, 1,3-nonadiene, 2,4-nonadiene, 3,5-nonadiene, 1,3-decadiene, 2,4-decadiene, 3,5-decadiene, or mixtures thereof, preferably 1,3-butadiene, 1,3-pentadiene, 2,4-hexadiene, or 1,3-hexadiene, and most preferably it is 1,3-butadiene. It is generally preferred that each of the (B) blocks is polymerized from a single monomer.

The scope of this embodiment, and of any other embodiments of the invention wherein the block (B) is used, also encompasses polymers wherein the block (B) may comprise copolymers of one or more conjugated diene of formula (3) and controlled amounts (about 0.3 to about 30 mole %) of an aryl-substituted olefin, e.g., styrene or other suitable monomers (such as alkylated styrene, vinyl naphthalene, or alkylated vinyl naphthalene) incorporated for control of glass transition temperature ($T_g$), density, solubility parameters and refractive index. Suitable aryl-substituted olefins are those described below in conjunction with another of the embodiments of the invention. Similarly, the scope of this embodiment also encompasses polymers wherein the block (B) may be comprised of copolymers of one or more conjugated diene of formula (3) and any other anionically polymerizable monomer capable of polymerizing with the conjugated diene of formula (3). Similar considerations also apply in the case of the (I) block(s), which can include similar styrene/diene copolymers.

The copolymer is polymerized by any conventional copolymerization process, preferably anionic polymerization, discussed in detail below. As will be apparent to those skilled in the art, the block copolymer of this embodiment contains at least two alternating blocks, (I)-(B) or (B)-(I), referred to herein as diblocks. The block copolymer of this embodiment may contain three alternating blocks, e.g., (I)-(B)-(I), referring to herein as triblocks or triblock units, but it may contain an unlimited number of blocks. The functionalization of any of these copolymers is conducted in a conventional manner and is described below.

After the (I)-(B) copolymer is polymerized, it is subjected to a selective hydrogenation reaction during which the polymerized conjugated dienes of formula (3) of the copolymer are selectively hydrogenated to such an extent that they contain substantially none of the original unsaturation, while the polymerized conjugated dienes of formula (1) of the copolymer retain a sufficient amount of their original unsaturation to permit functionalization.

Generally, for a copolymer wherein the conjugated dienes of formulae (1) and (3) are polymerized to provide unsaturation of formulae (2) and (4), respectively, as discussed above, the Iodine Number of the unsaturation of formula (2) after the selective hydrogenation reaction is from about 20% to about 100%, preferably from about 50% to about 100%, and most preferably about 100%, of the Iodine Number prior to the selective hydrogenation reaction; and for the unsaturation of formula (4) it is from about 0% to about 10%, preferably from about 0% to about 0.5%, and most preferably from about 0% to about 0.2%, of the Iodine Number prior to the selective hydrogenation reaction. The Iodine Number, as is known to those skilled in the art, is defined as the theoretical number of grams of iodine which will add to the unsaturation in 100 grams of olefin and is a quantitative measure of unsaturation.

In this embodiment of the invention, although the microstructure of the (I) blocks is not critical and may consist of 1,2-, 3,4- and/or 1,4-units, schematically represented below for the polyisoprene blocks, when a polar compound is used during the polymerization of the (I) block, the (I) blocks comprise primarily (at least about 50% wt.) 3,4-units, the rest being primarily (less than about 50% wt.) 1,4-units; when the polar compound is not used during the polymerization of the (I) block, the (I) blocks comprise primarily (about 80% wt.) 1,4-units, the rest being primarily 1,2- and 3,4-units.

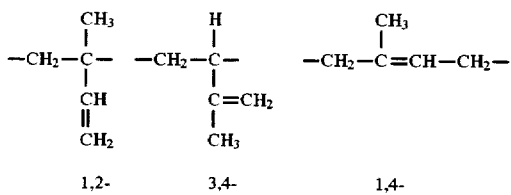

The microstructure of the (B) blocks, when the predominant monomer used to polymerize the (B) blocks is 1,3-butadiene, should be a mixture of 1,4- and 1,2-units schematically shown below for the polybutadiene blocks:

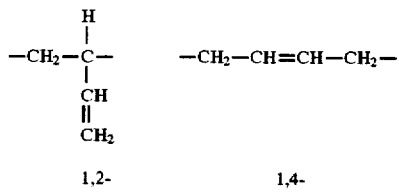

since the hydrogenation of the predominantly 1,4-microstructure produces a crystalline polyethylene segment. The microstructure of the (I) and (B) blocks (as well as of the polymerized conjugated dienes of formulae (1) or (3) in any polymers of this invention) is controlled in a conventional manner, e.g., by controlling the amount and nature of the polar compounds used during the polymerization reaction, and the reaction temperature. In one particularly preferred embodiment, the (B) block contains about 50% of the 1,2- and about 50% of the 1,4-microstructure. If the (B) block is poly-1,3-butadiene, the hydrogenation of the (B) segment containing from about 50% to about 60% of the 1,2-microstructure content produces an elastomeric center block which is substantially an ethylene-butene-1 copolymer having substantially no crystallinity. If the (B) block is polymerized from 1,3-pentadiene, it is preferred that it have predominantly (at least 50%) of 1,4-microstructure which, after hydrogenation, produces a substantially non-crystalline elastomeric block.

The terms "1,2-", "1,4-", and "3,4-microstructure" or "units" as used in this application refer to the products of polymerization obtained by the 1,2-, 1,4- and 3,4-, respectively, mode of addition of monomer units.

We surprisingly discovered that the polymerized conjugated dienes of formula (3), e.g., the dienes employed in (B) blocks, of the polymers of this invention are selectively hydrogenated in our hydrogenation process much faster than the polymerized conjugated dienes of formula (1), e.g., the dienes used in the (I) blocks. This is not evident from the teachings of Falk, discussed above, because Falk teaches that double bonds of the di-substituted 1,4-polybutadiene units are hydrogenated selectively in the presence of double bonds of the tri-substituted 1,4-polyisoprene units (which hydrogenate very slowly). We surprisingly discovered that the di-substituted double bonds of the 1,4-polybutadiene units are hydrogenated along with the monosubstituted double bonds of the 1,2-polybutadiene units, while the di-substituted double bonds of the 3,4-polyisoprene units are hydrogenated at a much slower rate than the aforementioned polybutadienes. Thus, in view of Falk's disclosure it is surprising that the di-substituted double bonds of the 1,4-polybutadiene units are hydrogenated selectively in the presence of the di-substituted double bonds of the 3,4-polyisoprene units. This is also surprising in view of the teaching of Hoxmeier, Published European Patent Application, Publication No. 0 315 280, who discloses that the di-substituted double bonds of the 1,4-polybutadiene units, monosubstituted double bonds of the 1,4-polybutadiene units and di-substituted double bonds of the 3,4-polyisoprene units are hydrogenated simultaneously at substantially the same rates. For example, for the block copolymers of this invention, wherein the (I) block is polyisoprene and the (B) block is polybutadiene. Fourier Transform Infrared (FTIR) analysis of selectively hydrogenated block copolymers of the invention, such as I-B-I triblock polymers, indicates that the hydrogenation of the double bonds of the 1,2-polybutadiene units proceeds most rapidly, followed by the hydrogenation of the double bonds of the 1,4-polybutadiene units. Infrared absorptions caused by these groups disappear prior to appreciable hydrogenation of the polyisoprene units.

Accordingly, by controlling the amount and placement of 1,2- versus 1,4-microstructure, as well as the amount and placement of polyisoprene units, it is now possible to control the amount and placement of unsaturation remaining in the polymers after hydrogenation. It follows that the mount and placement of functionalization of the polymeric dispersants of the invention is also controllable to an extent not possible previously.

After the block copolymer is prepared, it is subject to a selective hydrogenation reaction to hydrogenate primarily the (B) block(s). The selective hydrogenation reaction and the catalyst are described in detail below. After the hydrogenation reaction is completed, the selective hydrogenation catalyst is removed from the block copolymer, and the polymer is isolated by conventional procedures, e.g., alcohol flocculation, steam stripping of solvent, or non-aqueous solvent evaporation. An antioxidant, e.g., Irganox 1076 (from Ciba-Geigy), is normally added to the polymer solution prior to polymer isolation.

Copolymers of a Ring-Substituted Styrene and a Conjugated Diene

The present invention also includes copolymers that are prepared from at least one ring-substituted styrene and at least one conjugated diene, preferably p-methylstyrene and 1,3-butadiene. More specifically, the materials are generated by anionically polymerizing a ring-substituted styrene and a conjugated diene. The monomers can be polymerized either in block, tapered block, or random fashion. For a random distribution of the ring-substituted styrene, it is necessary to polymerize the two monomers in the presence of a substantial quantity of a polar modifier or to slowly add the diene to polymerizing ring-substituted styrene.

The scope of this embodiment includes polymers which include a ring-substituted styrene having at least one benzylic hydrogen and possessing the formula:

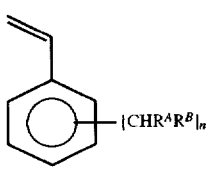

(5)

wherein n=1–5, and $R^A$ and $R^B$ are independently hydrogen or an alkyl group. Preferably, n=1–3, more preferably n=1. The ring-substituted styrene is preferably selected from p-alkylstyrenes, such as vinyl toluene, vinyl xylenes, methylstyrenes, ethylstyrenes, propylstyrenes, isopropylstyrenes, or sec-butylstyrenes, or benzyl styrenes; or a mixture thereof. Most preferably the ring-substituted styrene includes p-methylstyrene.

The conjugated diene in this embodiment may be selected from among the dienes having formula (1) or (3) as described elsewhere herein. Most preferably, the conjugated diene includes 1,3-butadiene.

Following polymerization the diene copolymer is preferably functionalized by a method which includes selectively hydrogenating the copolymer to provide a selectively hydrogenated copolymer, followed by functionalizing the selectively hydrogenated copolymer to provide a functionalized copolymer having at least one polar functional group.

The polymers of this embodiment preferably include a ring-substituted styrene in an amount of from about 0.5% wt. to about 25% wt., and a conjugated diene in an amount of from about 75% wt. to about 99.5% wt. More preferably, a ring-substituted styrene is included in an amount of from about 5% wt. to about 15% wt., and a conjugated diene in an amount of from about 85% to about 95% wt.

This embodiment includes block copolymers of a ring-substituted styrene and a conjugated diene, wherein the block copolymer includes at least two alternating blocks:

$(P)_x$-$(B)_y$ wherein the block (P) includes at least one polymerized ring-substituted styrene of formula (5) defined above, and the block (B) includes at least one polymerized conjugated diene of formula (1) or (3).

Preferably, in the block copolymers of this embodiment, x is from about 1 to about 600, and y is from about 30 to about 4,000, more preferably x is from about 1 to about 350, and y is from about 30 to about 2,800.

These copolymers, whether random, block or tapered block, linear, branched or star-branched, are preferably selectively hydrogenated according to the methods described elsewhere herein. The selective hydrogenation process operates to hydrogenate the original olefinic unsaturation in a controllable fashion, leaving the polymer with a selected amount of residual aromatic unsaturation. The selection of the conjugated diene in the polymer serves as a basis for controlling the rate and extent of hydrogenation of the polymer. Following hydrogenation, the Iodine Number of these polymers is from about 0% to about 1%, preferably from about 0% to about 0.4%, and more preferably from about 0% to about 0.1%, and most preferably about 0%, or the Iodine Number prior to the hydrogenation procedure.

The aromatic unsaturation, by contrast is preferably substantially retained following the selective hydrogenation. Preferably, following selective hydrogenation the polymer retains at least about 50% of its original aromatic unsaturation. More preferably, following selective hydrogenation the copolymer retains at least about 90% of its original aromatic unsaturation.

This embodiment also includes functionalized versions of the ring-substituted styrene-conjugated diene copolymers described above. Functionality-introducing reactions, preferably halogenation, followed by reaction with an amine or a polyamine, are carried out on the copolymers in a separate post-hydrogenation step.

Random Copolymers

Random copolymers of this invention have controlled amounts of unsaturation incorporated randomly in an otherwise saturated backbone. In contrast to EPDM, the level of unsaturation can be inexpensively and easily controlled, e.g., to produce polymers having Iodine Number of from about 5 to about 100, to provide a wide variation in the degree of functionalization.

In one embodiment, the random copolymers are polymerized from the same monomers used to polymerize the block copolymers $(I)_x$-$(B)_y$, described elsewhere herein. In particular, the random copolymers may be made by polymerizing at least one conjugated diene of formula (1) with at least one conjugated diene of formula (3), both defined above, provided that the diene of formula (1) is different from the diene of formula (3). This random copolymer contains from about 1.0% to about 40%, preferably from about 1.0% to about 20%, by mole of the polymerized conjugated diene of formula (1) and from about 60% to about 99%, preferably from about 80% to about 99% by mole of the polymerized conjugated diene of formula (3). Suitable conjugated dienes of formula (1) are exemplified above. The most preferred conjugated diene of formula (1) for the copolymerization of these random copolymers is isoprene. Suitable conjugated dienes of formula (3) are also exemplified above. 1,3-butadiene is the most preferred conjugated diene of formula (3) for the polymerization of the random copolymer of this embodiment. Thus, most preferably, in this embodiment, the random copolymer is polymerized from isoprene and 1,3-butadiene, and it contains from about 1% wt. to about 20% wt. of the isoprene units and form about 80% wt. to about 99% wt. of the butadiene units. The isoprene units have primarily (i.e., from about 50% wt. to about 90% wt.) the 3,4-microstructure.

In another embodiment, the random copolymers are polymerized from the same monomers used to polymerize the block copolymers $(P)_x$-$(B)_y$, described elsewhere herein. In this case, the random copolymers are made by polymerizing at least one ring-substituted styrene and at least one conjugated diene of formulae (1) or (3). The polymers of this embodiment preferably include a ring-substituted styrene in an amount of from about 0.5% wt. to about 25% wt., and a conjugated diene in an amount of from about 75% wt. to about 99.5% wt. More preferably, a ring-substituted styrene is included in an amount of from about 5% wt. to about 15% wt., and a conjugated diene in an amount of from about 85% to about 95% wt.

The random copolymers are subjected to the selective hydrogenation reaction discussed above for the block copolymers, during which polymerized conjugated diene units of formulae (1) or (3) are substantially completely hydrogenated, while the aromatic unsaturation is hydrogenated to a substantially lesser extent, i.e., to such an extent that they retain a sufficient amount of their original unsaturation to functionalize the copolymer, thereby producing dispersants and dispersant VI improvers having random unsaturation proportional to the unsaturation in the polymerized dienes of formula (1). For example, for random copolymer polymerized from a diene of formula (1) and a different diene of formula (3), the Iodine Number before selective hydrogenation for the polymer is about 450. After selective hydrogenation, the Iodine Number for the polymer is from about 10 to about 50, with most of the unsaturation being contributed by the diene of formula (1).

The hydrogenated polymers may be functionalized. The degree of functionalization of the polymers can be easily and inexpensively increased by increasing the content of the diene of formula (1), i.e., isoprene in the most preferred embodiment, in either embodiment of the random copolymers to from about 5% to about 20% by mole.

Star-Branched Polymers

The invention is also directed to star-branched block and random polymers. The star-branched block polymers are made from any combination of blocks (I) and (B) and (P), all defined above.

The star-branched (I)-(B) block polymers comprise from about 0.5% wt. to about 25% wt., preferably from about 1% wt. to about 5% wt., of the (I) blocks, and from about 75% wt. to about 99.5% wt., preferably from about 95% wt. to about 99% wt., of the (B) blocks.

The star-branched (P)-(B) block polymers comprise from about 0.5% wt. to about 25% wt., preferably from about 1% wt. to about 5% wt., of the (P) blocks, and from about 75% wt. to about 99.5% wt., preferably from about 95% wt. to about 99% wt., of the (B) blocks.

The star-branched block polymers are selectively hydrogenated in the selective hydrogenation process of this invention to such an extent that blocks (B) contain substantially none of the original unsaturation, while each of the blocks (I) respectively, retains a sufficient amount of the original unsaturation of the conjugated dienes present in these blocks to functionalize the star-branched block polymers. Thus, for the I-(B) star-branched block polymers, after the selective hydrogenation reaction, the Iodine Number for the (I) blocks is from about 10% to about 100%, preferably from about 25% to about 100%, more preferably from about 50% to about 100%, and most preferably about 100%, of the Iodine Number prior to the selective hydrogenation reaction; and for the (B) blocks it is from about 0% to about 10%, preferably from about 0% to about 0.5%, of the Iodine Number prior to the selective hydrogenation reaction.

Similarly, for the (P)-(B) star-branched block polymer, after the selective hydrogenation reaction, the Iodine Number for the (B) blocks is from about 0% to about 1%, preferably from about 0% to about 0.5%, and most preferably 0%, of the Iodine Number prior to the selective hydrogenation reaction. The (P) blocks preferably retain as much aromatic unsaturation as possible following hydrogenation. Preferably, the (P) block retain at least about 50%, more preferably at least about 90%, and most preferably about 100%, or their original aromatic unsaturation.

The star-branched random polymers are made from any combination of at least one diene of formula (1) and at least one diene of formula (3), different from the diene of formula (1), or from any combination of at least one ring-substituted styrene and at least one diene of formulae (1) or (3), all of which are the same as those discussed above. The star-branched random polymers of the dienes of formulae (1) and (3), which must be different from each other, comprise from about 1% wt. to about 25% wt., preferably from about 1% wt. to about 10% wt., of the diene of formula (1), and from about 75% wt. to about 99% wt., preferably from about 90% wt. to about 99% wt., of the diene of formula (3). The star-branched random polymers of the ring-substituted styrene and the diene of formulae (1) or (3) comprise from about 1% wt. to about 25% wt., preferably from about 1% wt. to about 10% wt., of the ring-substituted styrene, and from about 75% wt. to about 99% wt., preferably from about 90% wt. to about 99% wt., of the diene of formulae (1) or (3).

The star-branched random diene polymers are also selectively hydrogenated in the selective hydrogenation process of this invention to such an extent that the polymerized dienes of formula (3) contain substantially none of the original unsaturation, while the polymerized dienes of formula (1) retain a sufficient amount of the original unsaturation to functionalize the star-branched random polymers. Thus, for the star-branched random polymer of the conjugated diene of formula (1) and a different diene of formula (3), both identified above, the Iodine Number for the polymerized diene of formula (1), after the selective hydrogenation reaction, is from about 10% to about 100%, preferably from about 25% to about 100%, more preferably from about 50% to about 100%, and most preferably about 100%, of the Iodine Number prior to the selective hydrogenation reaction; and for the polymerized diene of formula (3) it is from about 0% to about 10%, preferably from about 0% to about 0.5%, of the Iodine Number prior to the selective hydrogenation reaction.

Homopolymers of a Conjugated Diene

The invention is further directed to diene homopolymers which have been partially hydrogenated such that they possess an iodine number of 1-150, preferably 2-100. The residual unsaturation is used to incorporate polar functionality along the backbone of the polymer. These functionalized materials may be used as lubricant additives. Functionalization may be accomplished as described herein, preferably by reacting with an unsaturated carboxylic acid derivative via the ene reaction or via a radical addition. The acylated polymer is preferably then further modifed by being reacted with a monoamine, a polyamine, a polyhydroxy compound, a reactive polyether, or a combination thereof. Other modification methods such as halogenation, epoxidation, hydroxylation, and the like, may be used.

The homopolymers and random copolymers of the invention are polymerized and/or coupled in a similar fashion, but all monomers, e.g., isoprene and butadiene, are mixed in a proper ratio prior to the reaction with the polar compound-modified alkyl-lithium. In homopolymer and random polymer preparation, of course, only one stage is necessary.

Polymerization Reaction

The polymers of this invention are polymerized by any known polymerization processes, preferably by an anionic polymerization process. Anionic polymerization is well known in the art and it is utilized in the production of a variety of commercial polymers. An excellent comprehensive review of the anionic polymerization processes appears in the text *Advances in Polymer Science* 56, "Anionic Polymerization", pp. 1–90, Springer-Verlag, Berlin, Heidelberg, New York, Tokyo 1984 in a monograph entitled *Anionic Polymerization of Non-polar Monomers Involving Lithium*, by R. N. Young, R. P. Quirk and L. J. Fetters, incorporated herein by reference. The anionic polymerization process is conducted in the presence of a suitable anionic catalyst (also known as an initiator), such as n-butyl-lithium, sec-butyl-lithium, t-butyl-lithium, sodium naphthalide or, cumyl potassium. The amount of the catalyst and the amount of the monomer in the polymerization reaction dictate the molecular weight of the polymer. The polymerization reaction is conducted in solution using an inert solvent as the polymerization medium, e.g., aliphatic hydrocarbons, such as hexane, cyclohexane, or heptane, or aromatic solvents, such as benzene or toluene. In certain instances, inert polar solvents, such as tetrahydrofuran, can be used alone as a solvent, or in a mixture with a hydrocarbon solvent.

The polymerization process will be exemplified below for the polymerization of one of the embodiments of the invention, and specifically for the preferred embodiment thereof, i.e., a triblock of polyisoprene-polybutadiene-polyisoprene. However, it will be apparent to those skilled in the art that the same process principles can be used for the polymerization of all polymers of the invention.

The process, when using a lithium-based catalyst, comprises forming a solution of the isoprene monomer in an inert hydrocarbon solvent, such as cyclohexane, modified by the presence therein of one or more polar compounds selected from the group consisting of ethers, thioethers, and tertiary amines, e.g., tetrahydrofuran. The polar compounds are necessary to control: the microstructure of the butadiene center block, i.e., the content of the 1,2-structure thereof. The higher the content of the polar compounds, the higher will be the content of the 1,2-structure in these blocks. Since the presence of the polar compound is not essential in the formation of the first polymer block with many initiators unless a high 3,4-structure content of the first block is desired, it is not necessary to introduce the polar compound at hits stage, since it may be introduced just prior to or together with the addition of the butadiene in the second polymerization stage. Examples of polar compounds which may be used are dimethyl ether, diethyl ether, ethyl methyl ether, ethyl propyl ether, dioxane, diphenyl ether, dipropyl ether, tripropyl amine, tributyl amine, trimethyl amine, triethyl amine, and N—N—N'—N'-tetramethyl ethylene diamine. Mixtures of the polar compounds may also be used. The amount of the polar compound depends on the type of the polar compound and the polymerization conditions as will be apparent to those skilled in the art. The effect of polar compounds on the polybutadiene microstructure is detailed in Antkowiak et al., "Temperature and Concentration Effects on Polar-modified Alkyl Lithium Polymerizations and Copolymerizations," *Journal of Polymer Science: Part A-1*, 10:1319–34 (1972), incorporated herein by reference. The polar compounds also accelerate the rate of polymerization. If monomers other than 1,3-butadiene, e.g., pentadiene, are used to polymerize the central blocks (B), polar compounds are not necessary to control the microstructure because such monomers will inherently produce polymers which do not possess crystallinity after hydrogenation.

When the alkyl lithium-based initiator, a polar compound and an isoprene monomer are combined in an inert solvent, polymerization of the isoprene proceeds to produce the first terminal block whose molecular weight is determined by the ratio of the isoprene to the initiator. The "living" polyisoprenyl anion formed in this first step is utilized as the catalyst for further polymerization. At this time, butadiene monomer is introduced into the system and block polymerization of the second block proceeds, the presence of the polar compound not influencing the desired degree of branching (1,2-structure) in the polybutadiene block. The resulting product is a living diblock polymer having a terminal anion and a lithium counterion. The living diblock polymer serves as a catalyst for the growth of the final isoprene block, formed when isoprene monomer is again added to the reaction vessel to produce the final polymer block, resulting in the formation of the I-B-I triblock. Upon completion of polymerization, the living anion, now present at the terminus of the triblock, is destroyed by the addition of a proton donor, such as methyl alcohol or acetic acid. The polymerization reaction is usually conducted at a temperature of between about 0° C. and about 100° C., although higher temperatures can be used. Control of a chosen reaction temperature is desirable since it can influence the effectiveness of the polar compound additive in controlling the polymer microstructure. The reaction temperature can be, for example, from about 50° C. to about 80° C. The reaction pressure is not critical and varies from about atmospheric to about 100 psig.

If the polar compounds are utilized prior to the polymerization of the first (I) segment, (I) blocks with high 3,4-unit content are formed. If polar compounds (some of which can be Lewis bases) are added after the initial (I) segment is prepared, the first (I) segment will possess a high percentage of 1,4-microstructure (which is tri-substituted), and the second (I) segment will have a high percentage of 3,4-microstructure.

The production of triblock polymers having a high 1,4-unit content on both of the terminal (I) blocks is also possible by the use of coupling techniques illustrated below for a polyisoprene-polybutadiene-polyisoprene block copolymer:

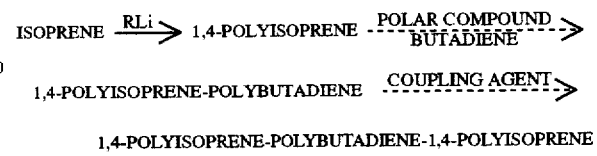

1,4-POLYISOPRENE-POLYBUTADIENE-1,4-POLYISOPRENE

The substitution of myrcene for the isoprene during the polymerization of the (I) blocks insures the incorporation of a high proportion of tri-substituted double bonds, even in the presence of polar compounds since myrcene contains a pendant tri-substituted double bond which is not involved in the polymerization process. In a coupling process, similar to that described above, block polymers containing polyisoprene end blocks (or any other polymerized monomer suitable for use in the (I) block) having a high 3,4-microstructure content can be obtained by adding the polar compound prior to the isoprene (or another monomer) polymerization.

The use of the coupling technique for the production of triblock polymers reduces the reaction time necessary for the completion of polymerization, as compared to sequential addition of isoprene, followed by butadiene, followed by isoprene. Such coupling techniques are well known and utilize coupling agents, such as esters, $CO_2$, iodine, dihaloalkanes, silicon tetrachloride, divinyl benzene, alkyl trichlorosilanes and dialkyl dichlorosilanes. The use of tri- or tetra-functional coupling agents, such as alkyl trichlorosilanes or silicon tetrachloride, permits the formation of macromolecules having 1- or 2- main chain branches, respectively. The addition of divinyl benzene as a coupling agent has been documented to produce molecules having up to 20 or more separately joined segments.

The use of some of the coupling agents provides a convenient means of producing star-branched block and random polymers. The star-branched block polymers are made from any combination of blocks (I) and (B), or (P) and (B), defined above. The star-branched random polymers are made from any combination of at least one diene of formula (1) and at least one diene of formula (3), different from the diene of formula (1), or from at least one aryl-substituted olefin, at least one diene of formula (1) and at least one diene of formula (3), different from the diene of formula (1). The molecular weight of the star-branched block and random copolymers will depend on the number of branches in each such copolymer, as will be apparent to those skilled in the art. Suitable coupling agents and reactions are disclosed in the following references which are incorporated herein by reference: U.S. Pat. Nos. 3,949,020; 3,594,452; 3,598,887; 3,465,065; 3,078,254; 3,766,301; 3,632,682; 3,668,279; and Great Britain patents 1,014,999; 1,074,276; 1,121,978.

Selective Hydrogenation

Following polymerization, selective hydrogenation of the polymer may be accomplished using techniques similar to those known in the art. A preferred method and catalyst are described in U.S. Pat. No. 5,187,236, the disclosure of which is incorporated herein by reference. The procedure and catalyst are described in greater detail below. In general, however, the previously described polymers can be contacted with hydrogen and a hydrogenation catalyst synthesized from a transition metal compound, typically nickel or cobalt, and a organometallic reducing agent, e.g., triethylaluminum. The hydrogenation proceeds at temperatures typically not in excess of about 40° C. and at pressures of from about 30 psi to about 200 psi. Generally, the polymers are hydrogenated such that substantially all of the unsaturation in formula (2) is removed, while much of that from formula (4) is retained. Alternatively, if it is desirable to functionalized one of the copolymers in a combined VI improver so as to provide the polymer with a secondary trait, e.g., antioxidancy or dispersancy, a selective hydrogenation may be performed leaving residual vinylidene or tri-substituted olefins from the isoprene which can later be modified. Any other known selective hydrogenation methods may be used, as will be apparent to those skilled in the art, but the method described above is one which is preferred.

The selective hydrogenation reaction will also be described below using a triblock of polyisoprene-polybutadiene-polyisoprene as an example. However, it will be apparent to those skilled in the art that any polymers of this invention can be selectively hydrogenated in the same manner.

The block copolymer is selectively hydrogenated to saturate the middle (polybutadiene) block of each of the triblocks. The method of selectively hydrogenating the polybutadiene block is similar to that of Falk, "Coordination Catalysts for the Selective Hydrogenation of Polymeric Unsaturation", *Journal of Polymer Science: Part A-1*, 9:2617–23 (1971), but it is conducted with a novel hydrogenation catalyst and process used herein. Any other known selective hydrogenation methods may also be used, as will be apparent to those skilled in the art, but it is preferred to use the method described herein. In summary, the selective hydrogenation method preferably used herein comprises contacting the previously-prepared block copolymer with hydrogen in the presence of the novel catalyst composition.

The novel hydrogenation catalyst composition and hydrogenation process are described in detail in previously cited application Ser. No. 07/466,136. The hydrogenation catalyst composition is synthesized from at least one transition metal compound and an organometallic reducing agent. Suitable transition metal compounds are compounds of metals of Group IVb, Vb, VIb or VIII, preferably IVb or VIII of the Period Table of the Elements, published in *Lange's Handbook of Chemistry*, 13th Ed. McGraw-Hill Book Company, New York (1985) (John A. Dean, ed.). Non-limiting examples of such compounds are metal halides, e.g., titanium tetrachloride, vanadium tetrachloride; vanadium oxytrichloride, titanium and vanadium alkoxides, wherein the alkoxide moiety has a branched or unbranched alkyl radical of 1 to about 20 carbon atoms, preferably 1 to about 6 carbon atoms. Preferred transition metal compounds are metal carboxylates or alkoxides of Group IVb or VIII of the Periodic Table of the Elements, such as nickel (II) 2-ethylhexanoate, titanium isopropoxide, cobalt (II) octoate, nickel (II) phenoxide and ferric acetylacetonate.

The organometallic reducing agent is any one or a combination of any of the materials commonly employed to activate Ziegler-Natta olefin polymerization catalyst components containing at least one compound of the elements of Groups Ia, IIa, IIb, IIIa, or IVa of the Period Table of the Elements. Examples of such reducing agents are metal alkyls, metal hydrides, alkyl metal hydrides, alkyl metal halides, and alkyl metal alkoxides, such as alkyllithium compounds, dialkylzinc compounds, trialkylboron compounds, trialkylaliminum compounds, alkylaluminum halides and hydrides, and tetraalkylgermanium compounds. Mixtures of the reducing agents may also be employed. Specific examples of useful reducing agents include n-butyllithium, diethylzinc, di-n-propylzinc, triethylboron, diethylaluminumethoxide, triethylaluminum, trimethylaluminum, triisobutylaluminum, tri-n-hexylaluminum, ethylaluminum dichloride, dibromide, and dihydride, isobutyl aluminum dichloride, dibromide, and dihydride, diethylaluminum chloride, bromide, and hydride, di-n-propylaluminum chloride, bromide, and hydride, diisobutylaluminum chloride, bromide and hydride, tetramethylgermanium, and tetraethylgermanium. Organometallic reducing agents which are preferred are Group IIIa metal alkyls and dialkyl metal halides having 1 to about 20 carbon atoms per alkyl radical. More preferably, the reducing agent is a trialkylaluminum compound having 1 to about 6 carbon atoms per alkyl radical. Other reducing agents which can be used herein are disclosed in Stevens et al., U.S. Pat. No. 3,787,384, column 4, line 45 to column 5, line 12 and in Strobel et al., U.S. Pat. No. 4,148,754, column 4, line 56 to column 5, line 59, the entire contents of both of which are incorporated herein by reference. Particularly preferred reducing agents are metal alkyl or hydride derivatives of a metal selected from Groups Ia, IIa and IIIa of the Period Table of the Elements, such as n-butyl lithium, sec-butyl lithium, n-hexyl lithium, phenyl-lithium, triethylaluminum, tri-isobutylaluminum, trimethylaluminum, diethylaluminum hydride and dibutylmagnesium.

The molar ratio of the metal derived from the reducing agent to the metal derived from the transition metal compound will vary for the selected combinations of the reducing agent and the transition metal compound, but in general it is about 1:1 to about 12:1, preferably about 1.5:1 to about 8:1, more preferably about 2:1 to about 7:1, and most preferably about 2.5:1 to about 6:1. It will be apparent to those skilled in the art that the optimal ratios will vary depending upon the transition metal and the organometallic agent used, e.g., for the trialkylaluminum/nickel(II) systems, the preferred aluminum:nickel molar ratio is about 2.5:1 to about 4:1, for the trialkylaluminum/cobalt(II) systems, the preferred aluminum:cobalt molar ratio is about 3:1 to about 4:1, and for the trialkylaluminum/titanium(IV) alkoxides systems, the preferred aluminum:titanium molar ratio is about 3:1 to about 6:1.

The mode of addition and the ratio of the reducing agent to the transition metal compound are important in the production of the novel hydrogenation catalyst having superior selectivity, efficiency and stability, as compared to prior art catalytic systems. During the synthesis of the catalysts it is preferred to maintain the molar ratio of the reactants used to synthesize the catalyst substantially constant. This can be done either by the addition of the reducing agent, as rapidly as possible, to a solution of the transition metal compound, or by a substantially simultaneous addition of the separate streams of the reducing agent and the transition metal compound to a catalyst synthesis vessel in such a manner that the selected molar ratios of the metal of the reducing agent to the metal of the transition metal compound are maintained substantially constant throughout substantially the entire time of addition of the two compounds. The time required for the addition must be such that excessive pressure and heat build-up are avoided, i.e., the temperature should not exceed about 80° C. and the pressure should not exceed the safe pressure limit of the catalyst synthesis vessel.

In a preferred embodiment, the reducing agent and the transition metal compound are added substantially simultaneously to the catalyst synthesis vessel in such a manner that the selected molar ratio of the reducing agent to the transition metal compound is maintained substantially constant during substantially the entire time of the addition of the two compounds. This preferred embodiment permits the control of the exothermic reaction so that the heat build-up is not excessive, and the rate of gas production during the catalyst synthesis is also non excessive—accordingly, the gas build-up is relatively slow. In this embodiment, carried out with or without a solvent diluent, the rate of addition of the catalysts components is adjusted to maintain the synthesis reaction temperature at or below about 80° C. which promotes the formation of the selective hydrogenation catalyst. Furthermore, the selected molar ratios of the metal of the reducing agent to the metal of the transition metal compound are maintained substantially constant throughout the entire duration of the catalyst preparation when the simultaneous mixing technique of this embodiment is employed.

In another embodiment, the catalyst is formed by the addition of the reducing agent to the transition metal compound. In this embodiment, the timing and the order of addition of the two reactants is important to obtain the hydrogenation catalyst having superior selectivity, efficiency and stability. Thus, in this embodiment, it is important to add the reducing agent to the transition metal compound in that order in as short a time period as practically possible. In this embodiment, the time allotted for the addition of the reducing agent to the transition metal compound is critical for the production of the novel catalyst. The term "as short a time period as practically possible" means that the time of addition is as rapid as possible, such that the reaction temperature is not higher than about 80° C. and the reaction pressure does not exceed the safe pressure limit of the catalyst synthesis vessel. As will be apparent to those skilled in the art, that time will vary for each synthesis and will depend on such factors as the types of the reducing agents, the transition metal compounds and the solvents used in the synthesis, as well as the relative amounts thereof, and the type of the catalyst synthesis vessel used. For purposes of illustration, a solution of about 15 mL of triethylaluminum in hexane should be added to a solution of nickel(II) octoate in mineral spirits in about 10-30 seconds. Generally, the addition of the reducing agent to the transition metal compound should be carried out in about 5 seconds (sec) to about 5 minutes (min), depending on the quantities of the reagents used. If the time period during which the reducing agent is added to the transition metal compound is prolonged, e.g., more than 15 minutes, the synthesized catalyst is less selective, less stable, and may be heterogeneous.

In the embodiment wherein the reducing agent is added as rapidly as possible to the transition metal compound, it is also important to add the reducing agent to the transition metal compound in the aforementioned sequence to obtain the novel catalyst. The reversal of the addition sequence, i.e., the addition of the transition metal compound to the reducing agent, or the respective solutions thereof, is detrimental to the stability, selectivity, activity, and homogeneity of the catalyst and is, therefore, undesirable.

In all embodiments of the hydrogenation catalyst synthesis, it is preferred to use solutions of the reducing agent and the transition metal compound in suitable solvents, such as hydrocarbon solvents, e.g., cyclohexane, hexane, pentane, heptane, benzene, toluene, or mineral oils. The solvents used to prepare the solutions of the reducing agent and of the transition metal compound may be the same or different, but if they are different, they must be compatible with each other so that the solutions of the reducing agent and the transition metal compound are fully soluble in each other.

The hydrogenation process comprises contacting the unsaturated polymer to be hydrogenated with an amount of the catalyst solution containing about 0.1 to about 0.5, preferably about 0.2 to about 0.3 mole percent of the transition metal based on moles of the polymer unsaturation. The hydrogen partial pressure is generally from about 5 psi to about several hundred psi, but preferably it is from about 10 psi to about 100 psi, the temperature of the hydrogenation reaction mixture is generally from about 0° C. to about 150° C., preferably from about 25° C. to about 80° C., more preferably from about 30° C. to about 60° C., since higher temperatures may lead to catalyst deactivation. The length of the hydrogenation reaction may be as short as 30 minutes and, as will be apparent to those skilled in the art, depends to a great extent on the actual reaction conditions employed. The hydrogenation process may be monitored by any conventional means, e.g., infra-red spectroscopy, hydrogen flow rate, total hydrogen consumption, or any combination thereof.

Upon completion of the hydrogenation process, unreacted hydrogen is either vented or consumed by the introduction of the appropriate amount of an unsaturated material, such as 1-hexene, which is converted to an inert hydrocarbon, e.g., hexane. Subsequently, the catalyst is removed from the resulting polymer solution by any suitable means, selected depending on the particular process and polymer. For a low molecular weight material, for example, catalyst residue removal may consist of a treatment of the solution with an oxidant, such as air, and subsequent treatment with ammonia and optionally methanol in amounts equal to the molar amount of the metals (i.e., the sum of the transition metal and the metal of the reducing agent) present in the hydrogenation catalyst to yield the catalyst residues as a filterable precipitate, which is filtered off. The solvent may then be removed by any conventional methods, such as vacuum stripping, to yield the product polymer as a clear, colorless fluid.

Alternatively, and in a preferred embodiment, upon completion of the hydrogenation reaction, the mixture is treated with ammonia in the molar amount about equal to that of the metals (i.e., the sum of the transition metal and the metal of the reducing agent) and aqueous hydrogen peroxide, in the molar amount equal to about one half to about one, preferably one half, of the amount of the metals. Other levels of the ammonia and peroxide are also operative, but those specified above are particularly preferred. In this method, a precipitate forms, which may be filtered off as described above.

In yet another alternative method the catalyst may be removed by extraction with an aqueous mineral acid, such as sulfuric, phosphoric, or hydrochloric acid, followed by washing with distilled water. A small amount of a material commonly used as an aid in removing transition metal-based catalysts, such as a commercially available high molecular weight diamine, e.g., Jeffamine D-2000 from Texaco, may be added to aid in phase separation and catalyst removal during the extractions. The resultant polymer solution is then dried over a drying agent, such as magnesium sulfate, separated from the drying agent and the solvent is then separated by any conventional methods, such as vacuum stripping, to yield a polymer as a clear fluid. Other method of polymer isolation, such as steam or alcohol flocculation, may be employed depending upon the hydrogenated polymer properties.

After hydrogenation and purification is complete, the polymer can be functionalized and used in the lubricant compositions of the invention: the liquids will serve as dispersants and the solids as dispersant VI improvers.

Functionalization of the Polymers

The unsaturated terminal blocks of the block polymers of this invention can be chemically modified to provide benefits which enhance the dispersancy and viscosity improving qualities of the materials of the invention. Such benefits may be obtained through methods similar to those employed for the modification of existing commercial materials, such as butyl rubber or EPDM.

Following the selective hydrogenation step, the remaining sites of unsaturation are chemically modified. Such methods include reacting the unsaturated groups in the polymer with any of various reagents to produce functional groups, such as hydroxyl, epoxy, sulfonic acid, mercapto, acrylate or carbonyl groups. Functionalization methods are well known in the art.

A preferred chemical modification method involves reaction of the polymer with an unsaturated carboxylic acid derivative, such as acrylic acid, maleic acid, fumaric acid, maleic anhydride, methacrylate, and the like. Most preferably, maleic anhydride is used for modification of unsaturation. Numerous methods are known for the modification of polybutene and EPDM via the ene reaction. Methods are also known for the reaction of maleic anhydride with EPM via a radical reaction in the presence of a radical initiator. These methods can be adapted to incorporate the unsaturated carboxylic acid derivatives into the polymeric dispersants of the invention.

In a preferred functionalization of diene copolymers, the selectively hydrogenated copolymer is functionalized with functional groups selected from among halogens, epoxies, sulfonic acids, and carboxylic acid derivatives, and subsequently modified further by reacting with a monoamine, a polyamine, or a polyhydroxy compound, a reactive polyether, or a combination thereof.

The ene reaction of maleic anhydride with materials of the invention can be performed on solutions of the polymers in light mineral oil or polyalphaolefin at temperatures of from about 150° C. to about 250° C., typically under in inert atmosphere. Such modification of the polymers of any embodiments of our invention occurs readily, since the residual isoprene unsaturation, primarily of the 3,4-type, illustrated above, is known to be more reactive with maleic anhydride than are the internal bonds found in EPDM.

Other functionality-introducing reactions such as halogenation may be carried out post-hydrogenation. Halogenation, preferably bromination, is made to occur by a radical reaction, wherein, heat, light, or a radical initiator, may be used. Halogenation processes are described, for example, in European Patent Application No. EP 0 344 021.

Subsequent to the acylation reaction (or other suitable modification as outlined above), the modified polymers are reacted with a Lewis base, such as a monoamine, a polyamine, a polyhydroxy compound, a reactive polyether, or a combination thereof. The amines which are useful for this modification reaction are characterized by the presence of at least one primary (i.e., $H_2N$—) or secondary (i.e., HN=) amino group. The monoamines and polyamines can be aliphatic amines, cycloaliphatic amines, heterocyclic amines, aromatic amines, or hydroxyamines. Preferably, the polyamines contain only one primary or secondary amine, with the remaining amines being tertiary (i.e., —N=) or aromatic amines. The amination can be accomplished by heating the maleic anhydride-modified diene polymer to about 150° C. in the presence of the amine, followed by stripping off the water. A useful monoamine is ethanol amine. Useful polyamines include aminopropylmorpholine and tetraethylenepentamine. Useful polyhydroxy compounds include ethylene glycol and pentaerythritol. Useful reactive polyethers include polyethers which contain hydroxy or amino groups which will react with the modified polymer, such as polyethylene glycol monoalcohol.

In addition, when the modified polymers react with an aromatic polyamine, the resultant dispersant has improved antioxidant properties.

With respect to polymers of the invention which include ring-substituted styrene units, in order to obtain exclusive substitution at the benzylic position, the polymers should not contain any in-chain (backbone) olefinic unsaturation. Halogenation may be accomplished by methods known in the art, such as the method described in European Patent Application No. EP 0 344 021. Chemical modification can then be accomplished by reacting the halogenated ring-substituted styrene-diene copolymer with the monoamine, polyamine, polyhydroxy compound, reactive polyether or a combination thereof.

The above description illustrates only some of the potentially valuable chemical modification of the polymers of this invention. The polymers of this invention provide a means for a wide variety of chemical modifications at selected sites in the polymer, e.g., only at the ends of a triblock polymer molecule (i.e., at the (I) blocks only), thereby presenting the opportunity to prepare materials previously impossible because of the lack of availability of such polymers. Some examples of well known chemical reactions which can be performed on polymers of this invention are found in E. M. Fetters, "Chemical Reactions of Polymers", *High Polymers*, Vol. 19, John Wiley, New York. (1964), incorporated herein by reference.

Dispersant and VI-Improving Applications

The polymers of the invention, whether block copolymers, tapered block copolymers, branched and star branched polymers, random copolymers, or homopolymers, have been unexpectedly found to have the capacity to modify the dispersancy and/or viscometric properties of fluids, such as mineral and synthetic oil lubricants and normally liquid fuels. Accordingly, it is within the scope of the invention that the dispersant polymers of the invention be employed in dispersant substances which can be added to fluids to modify the dispersancy and/or viscometric properties of the fluids. The invention, thus, also includes a method of modifying or improving the dispersancy and/or viscometric properties of a fluid by admixing with the fluid a sufficient amount of dispersant substance of the invention so as to obtain or provide a modified or improved fluid having modified or improved dispersancy and/or viscometric properties. Moreover, the invention also includes dispersant-modified or dispersant-improved fluids to which have been added a dispersant substance of the invention so as to modify the dispersancy and/or viscometric properties of the fluid.

The improvement of viscometric properties includes any one or more of the properties of fluids which are related to viscosity. The dispersant VI improvers of the invention specifically improve the viscosity index of such fluids. Viscosity index is a property characterizing the relationship between the viscosity of a fluid and temperature. Improvement in viscosity index is characterized by a decrease in the rate of change of viscosity per unit of temperature change. Typical properties which are modified or improved by the dispersant VI improvers of the invention include relative thickening power (RTP), borderline pumpability, permanent shear stability (DIN), temporary shear stability at low temperatures (CCS), and temporary shear stability at high temperatures (HTHS). Each of these properties can be determined or characterized by conventional methods.

The polymers of the invention may be employed as dispersants and/or dispersant VI improvers in a variety of lubricant fluids. Typically, such fluid is a mineral oil such as a mineral oil lubricant system, e.g., motor oils, automatic transmission fluids, tractor hydraulic fluids, gear oils, aviation oils, and the like. Other suitable applications include normally liquid fuels. The lubricant or fuel may be naturally occurring or synthetic, or a combination thereof. Natural oils include mineral oils obtained from petroleum, including distillate and residual lubricating oils, and the like. Synthetic oils can include synthetic hydrocarbon fluids e.g. PAOs, liquid esters, fluorocarbons, polyethers, polysilicones, and the like. The dispersants can be added to a lubricant or fuel formulation in any suitable and effective amount to modify the dispersancy and/or viscometric properties of the formulation. An examplary broad range is from about 0.001% wt. to about 20% wt., preferably from about 0.1% wt. to about 10% wt., more preferably from about 0.5% wt. to about 7% wt., of the formulation.

The polymers of the invention can be supplied neat or as an oil concentrate. Some of the polymers of the invention have cold flow properties, thereby making it difficult to transport such polymers except as a concentrate. However, for ease of handling, the polymers can be prepared as a liquid concentrate. Typically, such dispersant concentrates include a polymer of the invention in an amount of from about 5% wt. to about 90% wt., preferably from about 10% wt. to about 70% wt., of the concentrate.

In addition to the polymers described in this invention, the dispersant formulations and the fluid formulations can further include one or more additional additives known to those skilled in the art. Such additives include, for example, antioxidants, pour point depressants, detergents, dispersants, friction modifiers, anti-wear agents, VI improvers, anti-foam agents, corrosion and rust inhibitors, etc. Indeed, it is among the advantages of the compositions of the invention that they are unusually efficient modifiers of dispersancy and/or viscometric properties, such that in many cases significantly less of these additives need be added to achieve a desired combination of fluid properties. For example, the Examples below show, inter alia, that significant amounts of commercially available viscosity improvers can be displaced by adding a dispersant substance of the invention.

EXAMPLES

The following examples are intended to assist in a further understanding of the invention. The particular materials and conditions employed are intended to be further illustrative of the invention and are not limiting upon the reasonable scope thereof.

In all of the following examples, the experimental polymerization and functionalization work was performed with dried reactors and equipment and under strictly anaerobic conditions. Extreme care must be used to exclude air, moisture and other impurities capable of interfering with the delicate chemical balance involved in the synthesis of the polymers of this invention, as will be apparent to those skilled in the art.

The maleation process is described in Examples 5–7. Examples 8–23 describe the reaction of the acylated materials with Lewis bases to give the final dispersant.

Example 1

Preparation of 10,000-Molecular-Weight Isoprene-Butadiene (I-B) Polymers

A 5-gallon reactor was charged with 10.1 L of purified pentane under an inert atmosphere. To the reactor was added 632.5 g (9.29 mol) of purified isoprene, 62.2 ml of anhydrous tetrahydrofuran, and 10.0 ml of 2,2'-dipyridyl solution (0.1M) via a Hoke bomb. The reactor contents were heated to 50°–55° C. and titrated to a yellow-brown endpoint color with 1.6M n-butyllithium. The catalyst 1.6M n-butyllithium (263.5 ml, 0.421 mole) was then added to the reactor using a Hoke bomb. The polymerization reaction temperature was maintained between 50°–55° C. for 1 hour then cooled to 45°–50° C. At this time, 3584 g (66.4 mol) of freshly distilled butadiene was added. The polymerization continued for 0.5 hours, after which time 25.3 g (0.421 mol) of acetic acid was added. The molecular weight (Mn) was found to be approximately 10,000. An infrared analysis (FTIR) showed the butadiene microstructure to contain 55% 1,2- and 45% 1,4-microstructure.

Example 2

Preparation of 20,000-Molecular-Weight I-B Polymers

A 5-gallon reactor was charged with 10.1L of purified pentane under an inert atmosphere. To the reactor was added 421.6 g (6.19 mol) of purified isoprene, 62.2 ml of anhydrous tetrahydrofuran, and 10.0 ml 2,2'-dipyridyl solution (0.1M) via Hoke bomb. The reactor contents were heated to 50°–55° C. and titrated to a yellow-brown endpoint color with 1.6M n-butyllithium. The catalyst 1.6M n-butyllithium (131.8 ml, 0.211 mol) was then added to the reactor using a Hoke bomb. The polymerization reaction temperature was maintained between 50°–55° C. for 1 hour then cooled to 45°–50° C. At this time, 3794.9 g (70.3 mol) of freshly distilled butadiene was added. The polymerization continued for 30 minutes after which time 12.1 g (0.211 mol) of acetic acid was added. The molecular weight (Mn) was found to be approximately 20,000. An infrared analysis (FTIR) showed the butadiene microstructure to contain 55% 1,2- and 45% 1,4-microstructure.

Example 3

Hydrogenation of Example 1

The material prepared in Example 1 was hydrogenated by transferring the entire contents of the 5-gallon reactor to a 10-gallon reactor for hydrogenating. The reactor was pressured with hydrogen and released several times. The hydrogenation catalyst used was a 0.35M cobalt triethylaluminum complex where the ratio of aluminum to cobalt was 3.5:1. A Hoke bomb filled with 25 ml of catalyst was pressured with hydrogen. The contents were then transferred into the reactor. The reaction temperature was maintained at 50° C. and the infrared was used to monitor the disappearance of the unsaturation. When approximately 10 double bonds remained per polymer chain the reaction was stopped. The hydrogen was replaced with nitrogen. The contents of the reactor were diluted with 6 L of pentane and 21.4 ml of acetic acid were added along with 1.8 ml of a 30% hydrogen peroxide solution. The reactor contents were vigorously stirred and heated to 75° C. for 0.5 hours. After cooling to 30° C. and venting 15 psig, the solution was filtered. The liquid hydrogenated I-B polymer was finished by removing all volatiles.

Example 4

Hydrogenation of Example 2

The material prepared in Example 2 was hydrogenated by transferring the entire contents of the 5-gallon reactor to a 10-gallon reactor for hydrogenating. The reactor was pressured with hydrogen and released several times. The hydrogenation catalyst used was a 0.35M cobalt triethylaluminum complex where the ratio of aluminum to cobalt was 3.5:1. A Hoke bomb filled with 25 ml of catalyst was pressured with hydrogen. The contents were then transferred into the reactor. The reaction temperature was maintained at 50° C. and the infrared was used to monitor the disappearance of the unsaturation. When approximately 20 double bonds remained per polymer chain the reaction was stopped. The hydrogen was replaced with nitrogen. The contents of the reactor were diluted with 6 L of pentane and 21.4 ml of acetic acid were added along with 1.8 ml of a 30% hydrogen peroxide solution. The reactor contents were vigorously stirred and heated to 75° C. for 0.5 hours. After cooling to 30° C. and venting 15 psig, the solution was filtered. The liquid hydrogenated I-B polymer was finished by removing all volatiles.

Example 5

Maleic Modification of Example 3

The hydrogenated liquid I-B polymer from Example 3 was diluted (50/50) by mixing it with an equal amount of mineral oil (100N) to reduce the viscosity. A portion of this solution (3,563 g) was heated to 245°–250° C. in a 5-liter 4-neck round bottom flask fitted with a glass stirrer driven by an electric motor. The air in the flask was displaced with nitrogen gas; a nitrogen blanket was maintained on the flask at all time during the reaction by means of a positive flow of nitrogen gas through a mineral oil bubbler. Maleic anhydride (196 g) was gradually added to the reaction vessel. The contents of the flask were held under the same conditions overnight. The residual maleic anhydride was sparged out at 240° C. and a dark red brown viscous oil remained in the flask. This product was the maleated I-B elastomer with an acid number of 38 for the polymer (19 for the concentrate).

The acid number (mg. KOH per g. Sample) was determined by titration with alcoholic KOH using phenolphthalein as the indicator. It was calculated as follows: Acid Number={ |(ml. Of KOH)×(56.108)×(normality of KOH)|/|sample weight| }. The acid number is used to determine the percent of grafting efficiency of maleic anhydride onto the polymer backbone.

Example 6

Maleic Modification of Example 4

The hydrogenated liquid I-B polymer from Example 4 was diluted (50/50) by mixing it with an equal amount oil (100N) to reduce the viscosity. A portion of this solution (2,344 g) was heated to 245°–250° C. in a 5-liter 4-neck round bottom flask fitted with a glass stirrer driven by an electric motor. The air in the flask was displaced with nitrogen gas; a nitrogen blanket was maintained on the flask at all time during the reaction by means of a positive flow of nitrogen gas through a mineral oil bubbler. Maleic anhydride (164 g) was gradually added to the reaction vessel. The contents of the flask were held under the same conditions overnight. The residual maleic anhydride was sparged out at 240° C. and a dark red brown viscous oil remained in the flask. Because of extremely high viscosity of the reaction medium, 2,618 g of mineral oil was added thereby decreasing the solids level to about 25%. The acid number of the polymer in oil solution was 11.4 which means the polymer itself had an acid number of about 45 which equates to about 8.0% maleic anhydride in the polymer.

Example 7

Preparation of Maleated I-B Polymers

A liquid I-B polymer (with 15% isoprene, 50% vinyl content, MW=8,786) was diluted (50/50) by mixing it with an equal amount of mineral oil (100N) to reduce the viscosity. A 7,346 g portions of this mixture was combined with 293.8 g of maleic anhydride, 7.7 g of Irganox 1076, and 159.4 g of xylene in the 5-gallon autoclave. The air in the autoclave was displaced with nitrogen gas by several vacuum/nitrogen purge cycles. A nitrogen pressure (20–30 psi) was maintained at all time during the reaction. The contents of the vessel were heated to 195° C. and held under these conditions overnight. At the end of the reaction, residual maleic anhydride was stripped out under vacuum at 195° C. and a dark red brown viscous oil remained in the autoclave. This product was the maleated I-B polymer with an acid number of 36.

Example 8

Preparation of a Dispersant From Example 7

A mixture of 400 g of the maleated I-B polymer prepared in Example 7, 800 ml of toluene, 37.9 g of DA-14 (Tomah's ether diamine, 85% of isodecyloxypropylaminopropylamine, 5% of isodecyloxypropylamine, and 5% of alcohol, $C_9$–$C_{11}$ iso-$C_{10}$ rich), and 35.4 g of mineral oil were combined at room temperature in a 2,000-ml 4-neck round bottom flask fitted with a stirrer, a thermometer, nitrogen inlet tube, and a Dean-Stark trap with a condenser. The reaction mixture was heated to 110° C. and held overnight. The reaction mixture was stripped by heating it to 190° C. with a nitrogen sparge for 3 hours.

Example 9

Preparation of a Dispersant From Example 5

A mixture of 327 g of the maleated I-B polymer prepared in Example 5, 400 ml of toluene, 51 g of Union Carbide's polyethylene glycol monoalcohol, 60.6 g of mineral oil, and 0.04 g of dibutyltin oxide were added at room temperature to a 1,000-ml 4-neck round bottom flask fitted with stirrer, a thermometer, nitrogen inlet tube, and a Dean-Stark trap with a condenser. The reaction mixture was heated to 110° C. and held overnight. The reaction mixture was stripped by heating at 190° C. with a nitrogen sparge for 3 hours.

Example 10

Preparation of a Dispersant From Example 5

A mixture of 190.5 g of the maleated I-B polymer prepared in Example 5, 400 ml of toluene and 5.2 g of 4-(3-aminopropyl) morpholine and 39.9 g of mineral oil were added at room temperature to a 1,000-ml 4-neck round bottom flask fitted with a stirrer, a thermometer, nitrogen inlet tube, and a Dean-Stark trap with a condenser. The reaction mixture was heated to 110° C. and held for 3 hours. Subsequently, 25.2 g of Union Carbine's Carbowax MPEG-350 (polyethylene glycol monoalcohol) and 0.04 g of dibutyltin oxide were added to the reactor and the mixture was refluxed at 110° C. overnight. The reaction mixture was stripped by heating to 190° C. with a nitrogen sparge for 3 hours.

Example 11

Preparation of a Dispersant From Example 5

A mixture of 190.5 g of the maleated I-B polymer prepared in Example 5, 400 ml of toluene, 6.7 g of 3-dibutylaminopropylamine, and 41.4 g of mineral oil were added at room temperature to a 1,000-ml 4-neck round bottom flask fitted with a stirrer, a thermometer, nitrogen inlet tube, and a Dean-Stark trap with a condenser. The reaction mixture was heated to 110° C. and held for 3 hours. Subsequently, 25.2 go of Union Carbine's Carbowax MPEG-350 (polyethylene glycol monoalcohol) and 0.04 g of dibutyltin oxide was added to the reactor and the mixture was refluxed at 110° C. overnight. The reaction mixture was stripped by heating to 190° C. with a nitrogen sparge for 3 hours.

Example 12

Preparation of a Dispersant From Example 5

A mixture of 190.5 g of the maleated I-B polymer prepared in Example 5, 4000 ml of toluene, 3.4 g of N-phenyl-1,4-phenylenediamine and 51.2 g of mineral oil were added at room temperature to a 1,000-ml 4-neck round bottom flask fitted with a stirrer, a thermometer, nitrogen inlet tube, and a Dean-Stark trap with a condenser. The reaction mixture was heated to 110° C. and held for 3 hours. Subsequently, 38.3 g of Union Carbine's Carbowax MPEG-350 (polyethylene glycol monoalcohol) and 0.08 g of dibutyltin oxide were added to the reactor and the mixture was refluxed at 110° C. overnight. The reaction mixture was stripped by heating to 190° C. with nitrogen sparge for 3 hours.

Example 13

Preparation of a Dispersant From Example 5

A mixture of 190.5 g of the maleated I-B polymer prepared in Example 5, 400 ml of toluene, 6.7 g of N-phenyl-1,4-phenylenediamine and 41.7 g of mineral oil were added at room temperature to a 1,000-ml 4-neck round bottom flask fitted with a stirrer, a thermometer, nitrogen inlet tube, and a Dean-Stark trap with a condenser. The reaction mixture was heated to 110° C. and held for 3 hours. Subsequently, 25.5 g of Union Carbine's Carbowax MPEG-350 (polyethylene glycol monoalcohol) and 0.08 g of dibutylin oxide were added to the reactor and the mixture was refluxed at 110° C. overnight. The reaction mixture was stripped by heating to 190° C. with a nitrogen sparge for 3 hours.

Example 14

Preparation of a Dispersant From Example 6

A mixture of 32.7 g of the maleated I-B polymer prepared in Example 6, 400 ml of toluene, 3.0 g of N-phenyl-1,4-phenylenediamine and 87.4 g of mineral oil were added at room temperature to a 1,000-ml 4-neck round bottom flask fitted with a stirrer, a thermometer, nitrogen inlet tube, and a Dean-Stark trap with a condenser. The reaction mixture was heated to 110° C. and held for 3 hours. Subsequently, 34.4 g of Union Carbine's Carbowax MPEG-350 (polyethylene glycol monoalcohol) and 0.08 g of dibutyltin oxide were added to the reactor and the mixture was refluxed at 110° C. overnight. The reaction mixture was stripped by heating to 190° C. with a nitrogen sparge for 3 hours.

Example 15

Preparation of a Dispersant From Example 5

A mixture of 190.5 g of the maleated I-B polymer prepared in Example 5, 400 ml of Toluene, 3.4 g of N-phenyl-1,4-phenylenediamine and 20.7 g of mineral oil were added at room temperature to a 1,000-ml 4-neck round bottom flask fitted with a stirrer, a thermometer, nitrogen inlet tube, and a Dean-Stark trap with a condenser. The reaction mixture was heated to 110° C. and held for 3 hours. Subsequently, 7.9 g of 4-(3-aminopropyl) morpholine and 0.08 g of dibutyltin oxide were added to the reactor and the mixture was refluxed at 110° C. overnight. The reaction mixture was stripped by heating to 190° C. with a nitrogen sparge for 3 hours.

Example 16

Preparation of a Dispersant From Example 6

A mixture of 255 g of the maleated I-B polymer prepared in Example 6, 400 ml of toluene, 2.6 g of N-phenyl-1,4-phenylenediamine and 20.1 g of mineral oil were added at room temperature to a 1,000-ml 4-neck round bottom flask fitted with a stirrer, a thermometer, nitrogen inlet tube, and a Dean-Stark trap with a condenser. The reaction mixture was heated to 110° C. and held for 3 hours. Subsequently, 6.0 g of 4-(3-aminopropyl) morpholine and 0.08 g of dibutyltin oxide were added to the reactor and the mixture was refluxed at 110° C. overnight. The reaction mixture was stripped by heated to 190° C. with a nitrogen sparge.

Example 17

Preparation of a Dispersant From Example 5

A mixture of 190.5 g of the maleated I-B polymer prepared in Example 5, 400 ml of toluene, 6.7 g of N-phenyl-1,4-phenylenediamine and 2.6 g of 4-(3-aminopropyl)-morpholine, and 31.6 g of mineral oil were added at room temperature to a 1,000-ml 4-neck round bottom flask fitted with a stirrer, a thermometer, nitrogen

Example 18

Preparation of a Dispersant From Example 5

A mixture of 190.5 g of the maleated I-B polymer prepared in Example 5, 400 ml of toluene, 3.4 g of N-phenyl-1,4-phenylenediamine and 2.6 g of 4-(3-aminopropyl)-morpholine, and 41.0 g of mineral oil were added at room temperature to a 1,000-ml 4-neck round bottom flask fitted with a stirrer, a thermometer, nitrogen inlet tube, and a Dean-Stark trap with a condenser. The reaction mixture was heated to 110° C. and held for 3 hours. Subsequently, 25.5 g of Union Carbide's Carbowax MPEG-350 (polyethylene glycol monoalcohol) and 0.03 g of dibutyltin oxide were added to the reactor and the mixture was refluxed at 110° C. overnight. The reaction mixture was stripped by heating to 190° C. with a nitrogen sparge for 3 hours.

Example 19

Preparation of a Dispersant From Example 5

A mixture of 190.5 g of the maleated I-B polymer prepared in Example 5, 400 ml of toluene, 3.4 g of N-phenyl-1,4-phenylenediamine and 5.3 g of 4-(3-aminopropyl)-morpholine, and 30.9 g of mineral oil were added at room temperature to a 1,000-ml 4-neck round bottom flask fitted with a stirrer, a thermometer, nitrogen inlet tube, and a Dean-Stark trap with a condenser. The reaction mixture was heated to 110° C. and held for 3 hours. Subsequently, 12.8 g of Union Carbide's Carbowax MPEG-350 (polyethylene glycol monoalcohol) and 0.03 g of dibutyltin oxide were added to the reactor and the mixture was refluxed at 110° C. overnight. The reaction mixture was stripped by heating to 190° C. with a nitrogen sparge for 3 hours.

Example 20

Preparation of a Dispersant From Example 5

A mixture of 351.7 g of the maleated I-B polymer prepared in Example 6, 400 ml of toluene, 7.1 g of N-phenyl-1,4-phenylenediamine, 2.8 g of 4-(3-aminopropyl)-morpholine, and 54.4 g of mineral oil were added at room temperature to a 1,000-ml -4-neck round bottom flask fitted with a stirrer, a thermometer, nitrogen inlet tube, and a Dean-Stark trap with a condenser. The reaction mixture was heated to 110° C. and held for 3 hours. Subsequently, 13.5 g of Union Carbide's Carbowax MPEG-350 (polyethylene glycol monoalcohol) and 0.04 g of dibutyltin oxide were added to the reactor and the mixture was refluxed at 110° C. overnight. The reaction mixture was stripped by heating to 190° C. with a nitrogen sparge for 3 hours.

Example 21

Preparation of a Dispersant From Example 6

A mixture of 351.7 g of the maleated I-B polymer prepared in Example 6, 400 ml of toluene, 3.5 g of N-phenyl-1,4-phenylenediamine, 5.5 g of 4-(3-aminopropyl)-morpholine, and 52.5 g of mineral oil were added at room temperature to a 1,000-ml 4-neck round bottom flask fitted with a stirrer, a thermometer, nitrogen inlet tube, and a Dean-Stark trap with a condenser. The reaction mixture was heated to 110° C. and held for 3 hours. Subsequently, 13.4 g of Union Carbide's Carbowax MPEG-350 (polyethylene glycol monoalcohol) and 0.04 g of dibutyltin oxide were added to the reactor and the mixture was refluxed at 110° C. overnight. The reaction mixture was stripped by heating to 190° C. with a nitrogen sparge for 3 hours.

Example 22

Preparation of a Dispersant From Example 6

A mixture of 332 g of the maleated I-B polymer prepared in Example 6, 400 ml of toluene, 3.3 g of N-phenyl-1,4-phenylenediamine, 2.6 g of 4-(3-aminopropyl)-morpholine, and 73.2 g of mineral oil were added at room temperature to a 1,000-ml 4-neck round bottom flask fitted with a stirrer, a thermometer, nitrogen inlet tube, and a Dean-Stark trap with a condenser. The reaction mixture was heated to 110° C. and held for 3 hours. Subsequently, 25.4 g of Union Carbide's Carbowax MPEG-350 (polyethylene glycol monoalcohol) and 0.04 g of dibutyltin oxide were added to the reactor and the mixture was refluxed at 110° C. overnight. The reaction mixture was stripped by heating to 190° C. with a nitrogen sparge for 3 hours.

Example 23

Preparation of a Dispersant From Example 5

A mixture of 190.5 g of the maleated I-B polymer prepared in Example 5, 400 ml of toluene, 3.4 g of N-phenyl-1,4-phenylenediamine, 2.6 g of 4-(3-aminopropyl)-morpholine, and 3.4 g of 3-dibutylaminopropylamine diluted with 31.6 g of mineral oil were added at room temperature to a 1,000-ml 4-neck round bottom flask fitted with a stirrer, a thermometer, nitrogen inlet tube, and a Dean-Stark trap with a condenser. The reaction mixture was heated to 110° C. and held for 3 hours. Then, 12.8 g of Union Carbide's Carbowax MPEG-350 (polyethylene glycol monoalcohol) and 0.03 g of dibutyltin oxide was added into the reactor and refluxed at 110° C. overnight. The reaction mixture was stripped by heating to 190° C. with a nitrogen sparge for 3 hours.

Table 1 shows the molar composition of the materials prepared in Examples 8–23.

TABLE 1

% MOLAR COMPOSITION OF POLAR GROUPS

% MOLAR COMPOSITION

| Example No. | 3-Dibutylamino-propylamine | 4-(3-Aminopropyl)-Morpholine | Polyethylene Glycol Monoalcohol | N-Phenyl-1,4-Phenylenediamine |
|---|---|---|---|---|
| 8  | —  | —  | —   | —  |
| 9  | —  | —  | 100 | —  |
| 10 | —  | 33 | 67  | —  |
| 11 | 33 | —  | 67  | —  |
| 12 | —  | —  | 86  | 14 |
| 13 | —  | —  | 67  | 33 |
| 14 | —  | —  | 86  | 14 |
| 15 | —  | 75 | —   | 25 |
| 16 | —  | 75 | —   | 25 |
| 17 | —  | 20 | 40  | 40 |
| 18 | —  | 17 | 66  | 17 |
| 19 | —  | 40 | 40  | 20 |
| 20 | —  | 20 | 40  | 40 |
| 21 | —  | 40 | 40  | 20 |
| 22 | —  | 17 | 66  | 17 |
| 23 | 20 | 20 | 40  | 20 |

The Blotter Test is a traditional bench test for measuring the performance of dispersants. These dispersants were compared with a commercial dispersant, a succinimide-modified polyisobutylene. The performance of the dispersants of this invention at various treat rates is contrasted with that of the commercial product in Table 2 below. Percent dispersancy is reported as a number of 1 to 10, with the larger numbers corresponding to better dispersancy properties. The detailed procedure for the Blotter Test can be described as follows:

Procedure for the Blotter Test

A fully formulated oil containing all typical DII additives except dispersant is blended with the experimental or commercial dispersant at a level of 4% dispersant. This level may be reduced by diluting it with more of the oil to give 2%, 1% or 0.5% dispersant in oil. Into a glass vial, this test oil and used engine oil are weighed in a ratio of 1:2. The mixture is stirred vigorously and then heated in a 200C oven for 2 hours. Using a pipette, several drops of the mixture are dropped onto blotter paper and allowed to develop. The ratio of the inner diameter sludge circle to the outer diameter oil circle multiplied by 10 is the rating used.

Table 2 shows the Blotter Test results of the different dispersants prepared by reacting the maleated hydrogenated I-B copolymer with different polar components. The dispersants of this invention are clearly superior to the commercial dispersant exhibiting better dispersancy at equivalent treat rates in the Blotter Test. In addition, at lower treat rates (−50% less), dispersants of the invention are still superior to the commercial dispersant.

TABLE 2

BLOTTER RESULTS

TREAT RATE

| Example No. | 1.333% | 0.667% | 0.333% |
|---|---|---|---|
| 8  | 9 | 8 | 5 |
| 9  | 9 | 8 | 5 |
| 10 | 9 | 8 | 6 |
| 11 | 9 | 8 | 5 |

TABLE 2-continued

BLOTTER RESULTS

TREAT RATE

| Example No. | 1.333% | 0.667% | 0.333% |
|---|---|---|---|
| 12 | 9  | 8 | 6 |
| 13 | 9  | 7 | 6 |
| 14 | 9  | 8 | 6 |
| 15 | 9  | 9 | 8 |
| 16 | 10 | 9 | 7 |
| 17 | 9  | 8 | 5 |
| 18 | 9  | 8 | 5 |
| 19 | 9  | 8 | 6 |
| 20 | 9  | 8 | 7 |
| 21 | 9  | 9 | 7 |
| 22 | 9  | 8 | 7 |
| 23 | 10 | 9 | 8 |
| Commercial Dispersant | 8 | 6 | 4 |
| No Dispersant | 4 | 4 | 4 |

Table 3 shows the thermal properties of these dispersants measured by Different Scanning Calorimetry (DSC). The DSC results show how there is no thermal decomposition of the ashless dispersants containing an antioxidant group, e.g. N-phenyl-1,4-phenylenediamine, after 16 hours at 150° C. and 200 psig of oxygen. Paraffinic mineral oil (100 neutral) alone and the polymers of Examples 3–5 and 9 which do not contain aromatic diamines decompose in less than an hour. The polymers of Examples 12, 14–17, 20 and 23 which contain aromatic diamines showed no thermal decomposition after approximately 3 hours. The DSC results clearly demonstrate that these dispersants with aromatic polyamines have better oxidative stability than dispersants without the antioxidant appendages.

TABLE 3

THERMAL PROPERTIES

| Example No. | Thermal Decomposition/ Time (Minutes) |
| --- | --- |
| Mineral Oil | 31.31 min. |
| 3 | 33.29 min. |
| 4 | 36.21 min. |
| 5 | 48.41 min. |
| 9 | 34.92 min. |
| 12 | No* |
| 14 | No* |
| 15 | No* |
| 16 | No* |
| 17 | No* |
| 20 | No* |
| 23 | No* |

*After 160 Minutes

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

What is claimed is:

1. A dispersant substance for modifying the dispersancy or viscometric properties of a fluid, comprising:

a copolymer of a first conjugated diene and a second conjugated diene, wherein:
   said first conjugated diene comprises at least one relatively more substituted conjugated diene having at least five carbon atoms and the formula

(1)

wherein $R^1$—$R^6$ are each hydrogen or a hydrocarbyl group, provided that at least one of $R^1$-$R^6$ is a hydrocarbyl group, provided that after polymerization, the unsaturation of the polymerized conjugated diene of formula (1) has the formula:

(2)

wherein $R^I$, $R^{II}$, $R^{III}$ and $R^{IV}$ are each hydrogen or a hydrocarbyl group, provided that either both $R^I$ and $R^{II}$ are hydrocarbyl groups or both $R^{III}$ and $R^{IV}$ are hydrocarbyl groups; and said second conjugated diene comprises at least one relatively less substituted conjugated diene different from the first conjugated diene and having at least four carbon atoms and the formula:

(3)

wherein $R^9$-$R^{11}$ are each hydrogen or a hydrocarbyl group, provided that after polymerization, the unsaturation of the polymerized conjugated diene of formula (3) has the formula:

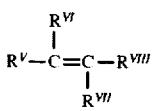

(4)

wherein $R^V$, $R^{VI}$, $R^{VII}$ and $R^{VIII}$ are each hydrogen or a hydrocarbyl group, provided that one of $R^V$ or $R^{VI}$ is hydrogen, one of $R^{VII}$ or $R^{VIII}$ is hydrogen, and at least one of $R^V$, $R^{VI}$, $R^{VII}$ and $R^{VIII}$ is a hydrocarbyl group; and wherein said copolymer has been functionalized by a method comprising:

selectively hydrogenating said copolymer to provide a selectively hydrogenated copolymer; and functionalizing said selectively hydrogenated copolymer to provide a functionalized copolymer having at least one polar functional group and modifying the functionalized copolymer by reaction with a Lewis base selected from the group consisting of a monoamine, polyamine, polyhydroxy compound, reactive polyether, or a combination thereof.

2. The dispersant substance of claim 1, wherein said first and second conjugated dienes are polymerized as a block copolymer comprising at least two alternating blocks:

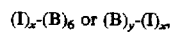

wherein:
   the block (I) comprises at least one polymerized conjugated diene of formula (1);
   the block (B) comprises at least one polymerized conjugated diene of formula (3));
   x is the number of polymerized monomer units in block (I) and is at least 1, and
   y is the number of polymerized monomer units in block (B) and is at least 25.

3. The dispersant substance of claim 1, wherein said first and second conjugated dienes are polymerized as a random copolymer.

4. The dispersant substance of claim 1, wherein said first and second conjugated dienes are polymerized as a branched or star-branched copolymer.

5. The dispersant substance of claim 1, wherein said copolymer has a molecular weight of at least about 2,000.

6. The dispersant substance of claim 5, wherein said copolymer has a molecular weight of from about 2,000 to about 1,000,000.

7. The dispersant substance of claim 6, wherein said copolymer has a molecular weight of from about 5,000 to about 500,000.

8. The dispersant substance of claim 1, wherein said first conjugated diene is included in said polymer in an amount of from about 0.5% wt. to about 25% wt.; and said second conjugated diene is included in said polymer in an amount of from about 75% wt. to about 99.5% wt.

9. The dispersant substance of claim 8, wherein said first conjugated diene is included in said polymer in an amount of from about 1% wt. to about 25% wt.; and said second conjugated diene is included in said polymer in an amount of from about 75% wt. to about 99% wt.

10. The dispersant substance of claim 2, wherein x is from about 1 to about 600, and y is from 30 to 4,000.

11. The dispersant substance of claim 10, wherein x is from about 1 to about 350, and y is from 30 to about 2,800.

12. The dispersant substance of claim 1, wherein said selectively hydrogenating step provides a selectively hydrogenated copolymer wherein the unsaturation of formula (4) is substantially completely hydrogenated to retain substantially none of the original unsaturation, while unsaturation of formula (2) retains a sufficient amount of its original unsaturation to permit said functionalizing of said copolymer.

13. The dispersant substance of claim 12, wherein after the selectively hydrogenating step, the Iodine Number for residual unsaturation of formula (2) is from about 50% to about 100% of the Iodine Number prior to the selectively hydrogenating step.

14. The dispersant substance of claim 13, wherein after the selectively hydrogenating step, the Iodine Number for residual unsaturation of formula (2) is about 100% of the Iodine Number prior to the selectively hydrogenating step.

15. The dispersant substance of claim 12, wherein after the selectively hydrogenating step, the Iodine Number for residual unsaturation of formula (4) is from about 0% to about 10% of the Iodine Number prior to the selectively hydrogenating step.

16. The dispersant substance of claim 15, wherein after the selectively hydrogenating step, the Iodine Number for residual unsaturation of formula (4) is from about 0% to about 0.5% of the Iodine Number prior to the selectively hydrogenating step.

17. The dispersant substance of claim 16, wherein after the selectively hydrogenating step, the Iodine Number for residual unsaturation of formula (4) is from about 0% to about 0.2% of the Iodine Number prior to the selectively hydrogenating step.

18. The dispersant substance of claim 1, wherein the conjugated diene of formula (1) comprises isoprene, 2,3-dimethyl-butadiene, 2-methyl-1,3-pentadiene, myrcene, 3-methyl-1,3-pentadiene, 4-methyl-1,3-pentadiene, 2-phenyl-1,3-butadiene, 2-phenyl-1,3-pentadiene, 3-phenyl-1,3 pentadiene, 2,3-dimethyl-1,3-pentadiene, 2-hexyl-1,3-butadiene, 3-methyl-1,3-hexadiene, 2-benzyl-1,3-butadiene, 2-p-tolyl-1,3-butadiene, or mixtures thereof.

19. The dispersant substance of claim 18, wherein the conjugated diene of formula (1) comprises isoprene, myrcene, 2,3-dimethyl-butadiene, or 2-methyl-1,3-pentadiene.

20. The dispersant substance of claim 19, wherein the conjugated diene of formula (1) comprises isoprene.

21. The dispersant substance of claim 1, wherein the conjugated diene of formula (3) comprises 1,3-butadiene, 1,3-pentadiene, 1,3-hexadiene, 1,3-heptadiene, 2,4-heptadiene, 1,3-octadiene, 2,4-octadiene, 3,5-octadiene, 1,3-nonadiene, 2,4-nonadiene, 3,5-nonadiene, 1,3-decadiene, 2,4-decadiene, 3,5-decadiene, or mixtures thereof.

22. The dispersant substance of claim 21, wherein the conjugate diene of formula (3) comprises 1,3-butadiene, 1,3-pentadiene, or 1,3-hexadiene.

23. The dispersant substance of claim 22, wherein the conjugated diene of formula (3) comprises 1,3-butadiene.

24. The dispersant substance of claim 2, wherein said conjugated diene of formula (3) comprises 1,3-butadiene, and each of the (B) blocks is a mixture of 1,4- and 1,2-units.

25. The dispersant substance of claim 24, wherein each of the (B) blocks has at least about 25% of the 1,2-units.

26. The dispersant substance of claim 25, wherein each of the (B) blocks has from about 30% of about 90% of the 1,2-subunits.

27. The dispersant substance of claim 26, wherein each of the (B) blocks has from about 45% to about 65% of the 1,2-units.

28. The dispersant substance of claim 1, wherein said functionalizing step provides a functionalized polymer having at least one functional group selected from the group consisting of halogen groups, hydroxyl groups, epoxy groups, sulfonic acid groups, mercapto groups, carboxylic acid groups, and mixtures thereof.

29. The dispersant substance of claim 28, wherein said functional group comprises an unsaturated carboxylic acid derivative group selected from the group consisting of acrylic acid, maleic acid, fumaric acid, maleic anhydride and methacrylic acid.

30. The dispersant substance of claim 29, wherein said functional group comprises maleic anhydride.

31. The dispersant substance of claim 28, wherein said functional group is selected from the group consisting of halogen groups, epoxy groups, sulfonic acid groups, and carboxylic acid derivative groups.

32. The dispersant substance of claim 1, wherein said functionalizing step comprises:

reacting said selectively hydrogenated copolymer with maleic anhydride to provide a maleated copolymer.

33. The dispersant substance of claim 1, wherein said polymer is distributed in a carrier fluid to provide a dispersant concentrate.

34. The dispersant substance of claim 33, wherein said polymer is included in an amount of from about 5% wt. to about 90% wt. of the dispersant concentrate.

35. The dispersant substance of claim 34, wherein said polymer is included in an amount of from about 10% wt. to about 70% wt. of the dispersant concentrate.

36. The dispersant substance of claim 1, further comprising at least one additive selected from the group consisting of antioxidants, pour point depressants, detergents, dispersants, friction modifiers, anti-wear agents, anti-form agents, corrosion and rust inhibitors, viscosity index improvers, and the like.

37. The dispersant substance of claim 1, wherein said Lewis base comprises an aromatic amine.

38. The dispersant substance of claim 1, wherein said Lewis base comprises a reactive polyether.

39. A method of modifying the dispersancy or viscometric properties of a fluid, comprising:

admixing with a fluid an amount of a dispersant substance sufficient to provide a dispersant-modified fluid having modified dispersant or viscometric properties; wherein said dispersant substance comprises:

a copolymer of a first conjugated diene and a second conjugate diene, wherein:

said first conjugated diene comprises at least one relatively more substituted conjugated diene having at least five carbon atoms and the formula:

wherein $R^1$–$R^4$ are each hydrogen or a hydrocarbyl group, provided that at least one of $R^1$–$R^6$ is a hydrocarbyl group, provided that after polymerization, the unsaturation of the polymerized conjugated diene of formula (1) has the formula:

wherein $R^I$, $R^{II}$, $R^{III}$ and $R^{IV}$ are each hydrogen or a hydrocarbyl group, provided that either both $R^I$ and $R^{II}$ are hydrocarbyl groups or both $R^{III}$ and $R^{IV}$ are hydrocarbyl groups; and said second conjugated diene comprises at least one relatively less substituted conjugated diene different from the first conjugated diene and having at least four carbon atoms and the formula:

wherein $R^7$–$R^{12}$ are each hydrogen or hydrocarbyl group, provided that after polymerization, the unsaturation of the polymerized conjugated diene of formula (3) has the formula:

wherein $R^V$, $R^{VI}$, $R^{VII}$ and $R^{VIII}$ are each hydrogen or a hydrocarbyl group, provided that one of $R^V$ or $R^{VI}$ is hydrogen, one of $R^{VII}$ or $R^{VIII}$ is hydrogen, and at least one of $R^V$, $R^{VI}$, $R^{VII}$ and $R^{VIII}$ is a hydrocarbyl group; and wherein said copolymer has been functionalized by a method comprising:

selectively hydrogenating said copolymer to provide a selectively hydrogenated copolymer; and functionalizing said selectively hydrogenated copolymer to provide a functionalized copolymer having at least one polar functional group and modifying the functionalized copolymer by reaction with a Lewis base selected from the group consisting of a monoamine, polyamine, polyhydroxy compound, reactive polyether, or a combination thereof.

40. The method of claim 19, comprising admixing said dispersant substance in an amount of from about 0.001% wt. to about 20% wt. of said dispersant-modified fluid.

41. The method of claim 40, comprising admixing said dispersant substance in an amount of from about 0.1% wt. to about 10% wt. of said dispersant-modified fluid.

42. The method of claim 41, comprising admixing said dispersant substance in an amount of from about 0.5% wt. to about 5% wt. of said dispersant-modified fluid.

43. The method of claim 39, wherein said fluid is selected from the group consisting of motor oils, transmission fluids, hydraulic fluids, gear oils, aviation oils, normally liquid fuels, and the like.

44. The method of claim 39, further comprising admixing with said fluid at least one additive selected from the group consisting of antioxidants, pour point depressants, detergents, dispersants, friction modifiers, anti-wear agents, anti-foam agents, corrosion and rust inhibitors, viscosity index improvers, and the like.

45. A dispersant-modified fluid having modified dispersancy or viscometric properties comprising:

a fluid; and a dispersant substance comprising:

a copolymer of a first conjugated diene and a second conjugated diene, wherein:

said first conjugated diene comprises at least one relatively more substituted conjugated diene having at least five carbon atoms and the formula:

wherein $R^1$–$R^6$ are each hydrogen or a hydrocarbyl group, provided that at least one of $R^1$–$R^4$ is a hydrocarbyl group, provided that after polymerization, the unsaturation of the polymerized conjugated diene of formula (1) has the formula

wherein $R^I$, $R^{II}$, $R^{III}$ and $R^{IV}$ are each hydrogen or a hydrocarbyl group, provided that either both $R^I$ and $R^{II}$ are hydrocarbyl groups or both $R^{III}$ and $R^{IV}$ are hydrocarbyl groups; and said second conjugated diene comprises at least one relatively less substituted conjugated diene different from the first conjugated diene and having at least four carbon atoms and the formula:

wherein $R^7$–$R^{12}$ are each hydrogen or a hydrocarbyl group, provided that after polymerization, the unsaturation of the polymerized conjugated diene of formula (3) has the formula:

wherein $R^V$, $R^{VI}$, $R^{VII}$ and $R^{VIII}$ are each hydrogen or a hydrocarbyl group, provided that one of $R^V$ or $R^{VI}$ is hydrogen, one of $R^{VII}$ or $R^{VIII}$ is hydrogen, and at least one of $R^V$, $R^{VI}$, $R^{VII}$ and $R^{VIII}$ is a hydrocarbyl group; and wherein said copolymer has been functionalized by a method comprising:

selectively hydrogenating said copolymer to provide a selectively hydrogenated copolymer; and functionalizing said selectively hydrogenated copolymer to provide a functionalized copolymer having at least one polar functional group modifying the functionalized copolymer by reaction with a Lewis base selected from the group consisting of a monoamine, polyamine, polyhydroxy compound, reactive polyether, or a combination thereof.

46. The dispersant-modified fluid of claim 45, wherein said dispersant substance is included in an amount of from about 0.001% wt. to about 20% wt.

47. The dispersant-modified fluid of claim 46, wherein said dispersant substance is included in an amount of from about 0.1% wt. to about 10% wt.

48. The dispersant-modified fluid of claim 46, wherein said dispersant substance is included in an amount of from about 0.5% wt. to about 5% wt.

49. The dispersant-modified fluid of claim 48, wherein said fluid is selected from the group consisting of motor oils, transmission fluids, hydraulic fluids, gear oils, aviation oils, normally liquid fuels, and the like.

50. The dispersant-modified fluid of claim 45, wherein said lubricant fluid further comprises at least one additive selected from the group consisting of antioxidants, pour point depressants, detergents, dispersants, friction modifiers, anti-wear agents, anti-foam agents, corrosion and rust inhibitors, viscosity index improvers, and the like.

51. A dispersant substance for modifying the dispersancy or viscometric properties of a lubricant fluid, comprising:

a homopolymer of a conjugated diene, wherein:
said conjugated diene has at least five carbon atoms and the formula:

(1)

wherein $R^1$–$R^6$ are each hydrogen or a hydrocarbyl group, provided that at least one of $R^1$–$R^6$ is a hydrocarbyl group, provided that after polymerization, the unsaturation of the polymerized conjugated diene of formula (1) has the formula:

(2)

wherein $R^I$, $R^{II}$, $R^{III}$ and $R^{IV}$ are each hydrogen or a hydrocarbyl group, provided that either both $R^I$ and $R^{II}$ are hydrocarbyl groups or both $R^{III}$ and $R^{IV}$ are hydrocarbyl groups; or said conjugated diene has at least four carbon atoms and the formula:

(3)

wherein $R^7$–$R^{12}$ are each hydrogen or a hydrocarbyl group, provided that after polymerization, the unsaturation of the polymerized conjugated diene of formula (3) has the formula:

(4)

wherein $R^V$, $R^{VI}$, $R^{VII}$ and $R^{VIII}$ are each hydrogen or a hydrocarbyl group, provided that one of $R^V$ and $R^{VI}$ is hydrogen, one of $R^{VII}$ or $R^{VIII}$ is hydrogen, and at least one of $R^V$, $R^{VI}$, $R^{VII}$ and $R^{VIII}$ is a hydrocarbyl group;

wherein said polymer has been functionalized by a method comprising:

partially hydrogenating said polymer to provide a partially hydrogenated polymer; and functionalizing said partially hydrogenated polymer to provide a functionalized polymer having at least one polar functional group and modifying the functionalized copolymer by reaction with a Lewis base selected from the group consisting of a monoamine, polyamine, polyhydroxy compound, reactive polyether, or a combination thereof.

52. The dispersant substance of claim 51, wherein said functionalizing step includes modifying said partially hydrogenated polymer to provide said functionalized polymer having at least one functional group selected from the group consisting of halogen groups, hydroxyl groups, epoxy groups, sulfonic acid groups, mercapto groups, carboxylic acid derivative groups, and mixtures thereof.

53. The dispersant substance of claim 52, wherein said Lewis base comprises an aromatic amine.

54. The dispersant substance of claim 52, wherein said Lewis base comprises a reactive polyether.

55. The dispersant substance of claim 50, wherein said polymer is distributed in a carrier fluid to provide a dispersant concentrate.

56. A method of modifying the dispersancy or viscometric properties of a fluid, comprising:

admixing with a fluid an amount of a dispersant substance sufficient to provide a fluid having modified dispersancy or viscometric properties;

wherein said dispersant substance comprises:

a homopolymer of a conjugated diene, wherein:
said conjugated diene has at least five carbon atoms and the formula:

(1)

wherein $R^1$–$R^6$ are each hydrogen or a hydrocarbyl group, provided that at least one of $R^1$–$R^6$ is a hydrocarbyl group, provided that after polymerization, the unsaturation of the polymerized conjugated diene of formula (1) has the formula:

(2)

wherein $R^I$, $R^{II}$, $R^{III}$ and $R^{IV}$ are each hydrogen or a hydrocarbyl group, provided that either both $R^I$ and $R^{II}$ are hydrocarbyl groups or both $R^{III}$ and $R^{IV}$ are hydrocarbyl groups; or said conjugated diene has at least four carbon atoms and the formula:

(3)

wherein $R^7$–$R^{12}$ are each hydrogen or a hydrocarbyl group, provided that after polymerization, the unsaturation of the polymerized conjugated diene of formula (3) has the formula:

(4)

wherein $R^V$, $R^{VI}$, $R^{VII}$ and $R^{VIII}$ are each hydrogen or a hydrocarbyl group, provided that one of $R^V$ or $R^{VI}$ is hydrogen, one of $R^{VII}$ or $R^{VIII}$ is hydrogen, and at least one of $R^V$, $R^{VI}$, $R^{VII}$ and $R^{VIII}$ is a hydrocarbyl group;

wherein said polymer has been functionalized by a method comprising:

selectively hydrogenating said polymer to provide a partially hydrogenated polymer; and functionalizing said partially hydrogenated polymer to provide a functionalized polymer having at least one polar functional group and modifying the functionalized copolymer by reaction with a Lewis base selected from the group consisting of a monoamine, polyamine, polyhydroxy compound, reactive polyether, or a combination thereof.

57. A dispersant-modified fluid having a modified dispersancy or viscometric properties, comprising:

a fluid; and a dispersant substance comprising:

a homopolymer of a conjugated diene, wherein:
said conjugated diene has at least five carbon atoms and the formula:

$$R^1-C=C-C=C-R^6 \quad (1)$$
$$\phantom{R^1-C=}\,|\phantom{=}\,|\phantom{-C=}\,|\phantom{=}\,|$$
$$\phantom{R^1-C=}R^2\ R^3\ R^4\ R^5$$

wherein $R^1$–$R^6$ are each hydrogen or a hydrocarbyl group, provided that at least one of $R^1$–$R^6$ is a hydrocarbyl group, provided that after polymerization, the unsaturation of the polymerized conjugated diene of formula (1) has the formula:

$$\begin{array}{c} R^{II} \\ | \\ R^{I}-C=C-R^{III} \\ | \\ R^{IV} \end{array} \quad (2)$$

wherein $R^I$, $R^{II}$, $R^{III}$ and $R^{IV}$ are each hydrogen or a hydrocarbyl group, provided that either both $R^I$ and $R^{II}$ are hydrocarbyl groups or both $R^{III}$ and $R^{IV}$ are hydrocarbyl groups; or said conjugated diene has at least four carbon atoms and the formula:

$$R^7-C=C-C=C-R^{12} \quad (3)$$
$$\phantom{R^7-C=}\,|\phantom{=}\,|\phantom{-C=}\,|\phantom{=}\,|$$
$$\phantom{R^7-C=}R^8\ R^9\ R^{10}\ R^{11}$$

wherein $R^7$–$R^{12}$ are each hydrogen or a hydrocarbyl group, provided that after polymerization, the unsaturation of the polymerized conjugated diene of formula (3) has the formula:

$$\begin{array}{c} R^{VI} \\ | \\ R^V-C=C-R^{VIII} \\ | \\ R^{VII} \end{array} \quad (4)$$

wherein $R^V$, $R^{VI}$, $R^{VII}$ and $R^{VIII}$ are each hydrogen or a hydrocarbyl group, provided that one of $R^V$ or $R^{VI}$ is hydrogen, one of $R^{VII}$ or $R^{VIII}$ is hydrogen and at least one of $R^V$, $R^{VI}$, $R^{VII}$ and $R^{VIII}$ is a hydrocarbyl group;

wherein said polymer has been functionalized by a method comprising:

selectively hydrogenating said polymer to provide a partially hydrogenated polymer; and functionalizing said partially hydrogenated polymer to provide a functionalized polymer having at least one polar functional group and modifying the functionalized copolymer by reaction with a Lewis base selected from the group consisting of a monoamine, polyamine, polyhydroxy compound, reactive polyether, or a combination thereof.

* * * * *

UNITED STATES PATENT AND TRADEMARK OFFICE
CERTIFICATE OF CORRECTION

PATENT NO. : 5,780,540

DATED : July 14, 1998

INVENTOR(S) : Ellen B. Brandes et al.

It is certified that error appears in the above-identified patent and that said Letters Patent is hereby corrected as shown below:

In the Claims:

Column 44, line 27 " $(I)_x-(B)_6$ or $(B)_y-(I)_x$," should be ---" $(I)_x-(B)_y$ or $(B)_y-(I)_x$,---

Column 46, line 54 "$R^1-R^4$" should be --- $R^1-R^6$ ---.

Column 47, line 34 "claim 19" should be --claim 39---.

Column 47, line 67 "$R^1-R^4$" should be ---$R^1-R^6$---.

Column 48, line 53 "claim 46" should be ---claim 47---.

Signed and Sealed this

Sixth Day of October, 1998

Attest:

Attesting Officer

BRUCE LEHMAN

Commissioner of Patents and Trademarks